(12) United States Patent
Maeda et al.

(10) Patent No.: US 8,465,488 B2
(45) Date of Patent: Jun. 18, 2013

(54) ENDOSCOPIC SURGICAL INSTRUMENT

(75) Inventors: Seiji Maeda, Kunitachi (JP); Hideyuki Kasahara, Hamura (JP); Ken Yamatani, Fuchu (JP); Akihito Kano, Hino (JP); Randal James Kadykowski, South Lyon, MI (US); Lyne Madeleine Charron-Keller, Brighton, MI (US)

(73) Assignees: Olympus Medical Systems Corporation, Tokyo (JP); Terumo Cardiovascular Systems Corporation, Ann Arbor, MI (US)

( * ) Notice: Subject to any disclaimer, the term of this patent is extended or adjusted under 35 U.S.C. 154(b) by 685 days.

(21) Appl. No.: 12/724,757

(22) Filed: Mar. 16, 2010

(65) Prior Publication Data
US 2011/0230881 A1 Sep. 22, 2011

(51) Int. Cl.
*A61B 18/18* (2006.01)

(52) U.S. Cl.
USPC .................................. 606/46; 606/48; 606/50

(58) Field of Classification Search
USPC ......................................... 606/45, 46, 48–50
See application file for complete search history.

(56) References Cited

U.S. PATENT DOCUMENTS

| | | | |
|---|---|---|---|
| 6,135,999 A | 10/2000 | Fanton et al. | |
| 6,461,357 B1 | 10/2002 | Sharkey et al. | |
| 7,850,687 B2 | 12/2010 | Kasahara | |
| 2003/0130654 A1* | 7/2003 | Kasahara et al. | 606/45 |
| 2005/0148817 A1* | 7/2005 | Kasahara et al. | 600/114 |
| 2005/0149094 A1* | 7/2005 | Kasahara et al. | 606/185 |
| 2005/0154257 A1* | 7/2005 | Kasahara et al. | 600/114 |
| 2005/0203441 A1 | 9/2005 | Voegele | |
| 2006/0206112 A1* | 9/2006 | Kasahara | 606/45 |
| 2006/0211916 A1* | 9/2006 | Kasahara et al. | 600/114 |
| 2006/0235450 A1* | 10/2006 | Kasahara et al. | 606/159 |
| 2009/0024121 A1* | 1/2009 | Kasahara et al. | 606/39 |
| 2011/0230711 A1* | 9/2011 | Kano et al. | 600/104 |

FOREIGN PATENT DOCUMENTS

| | | |
|---|---|---|
| JP | 8-317935 | 12/1996 |
| JP | 200070280 | 3/2000 |
| JP | 200161848 | 3/2001 |
| JP | 2003199766 A | 7/2003 |
| JP | 2003290248 A | 10/2003 |
| JP | 2003305054 | 10/2003 |
| JP | 2006280662 | 10/2006 |
| JP | 2006326157 | 12/2006 |
| WO | 9724074 | 7/1997 |

* cited by examiner

*Primary Examiner* — Linda Dvorak
*Assistant Examiner* — Jocelyn D Ram
(74) *Attorney, Agent, or Firm* — Gael Diane Tisack; Darryl Newell; MacMillan, Sobanski & Todd, LLC

(57) ABSTRACT

An endoscopic surgical instrument includes an insertion section which is inserted into a body cavity, and a surgical section which is disposed on a tip of the insertion section and treats an object. The surgical section includes a body section, and a first electrode, a second electrode, and a third electrode which are disposed on the body section. The surgical section coagulates and cuts the object by using a combination of not less than two of the first electrode, the second electrode, and the third electrode.

8 Claims, 20 Drawing Sheets

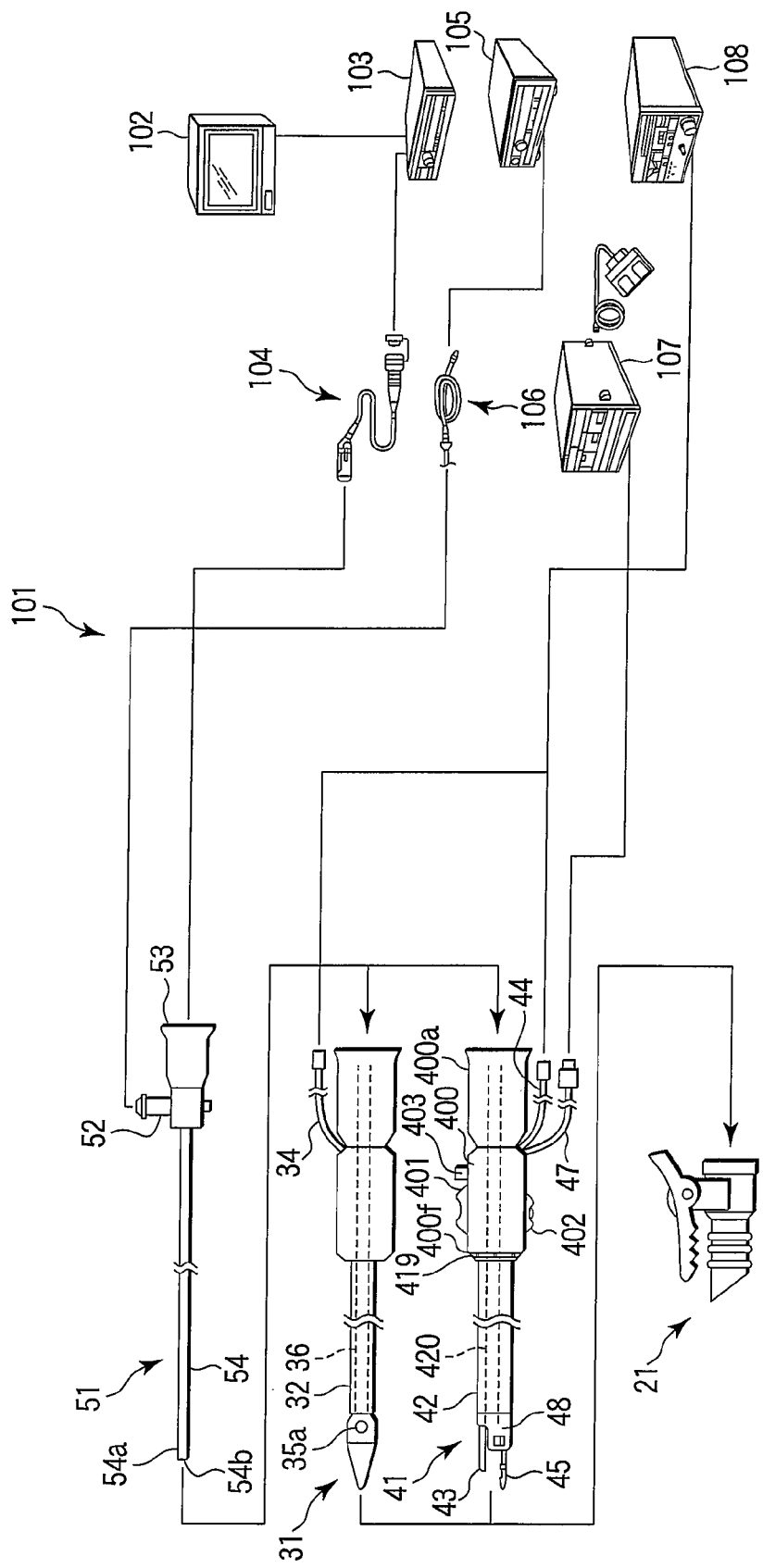
F I G. 1

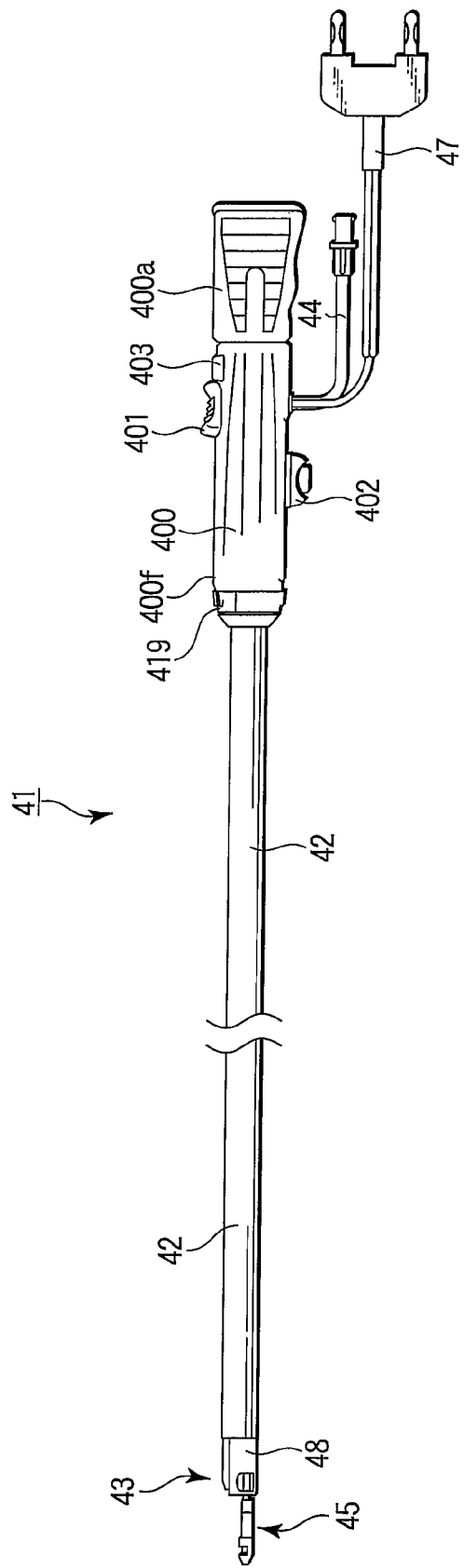
F I G. 2B

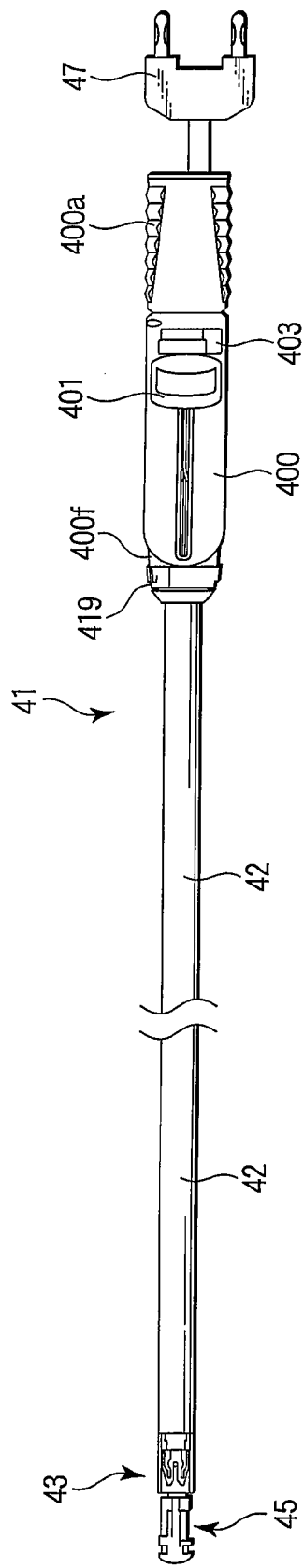
F I G. 2C

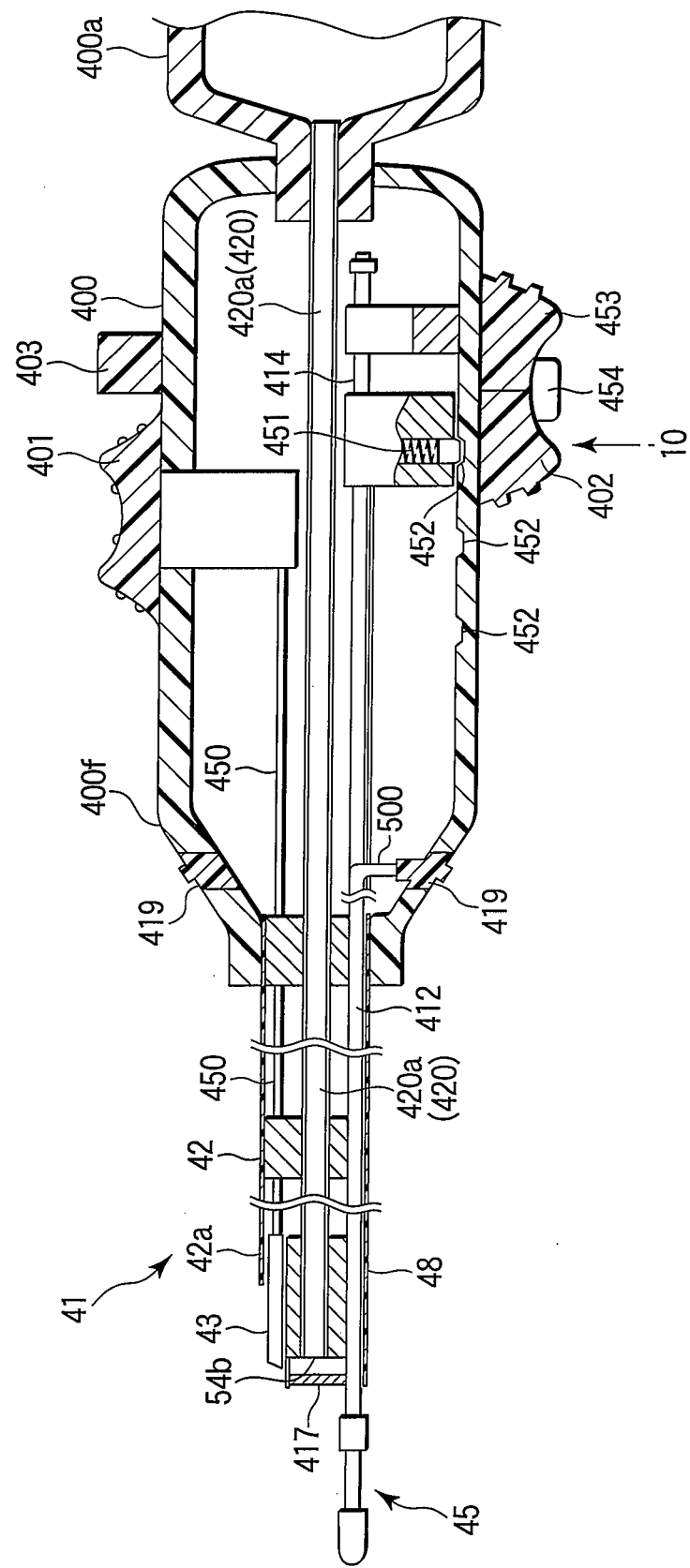
F I G. 6

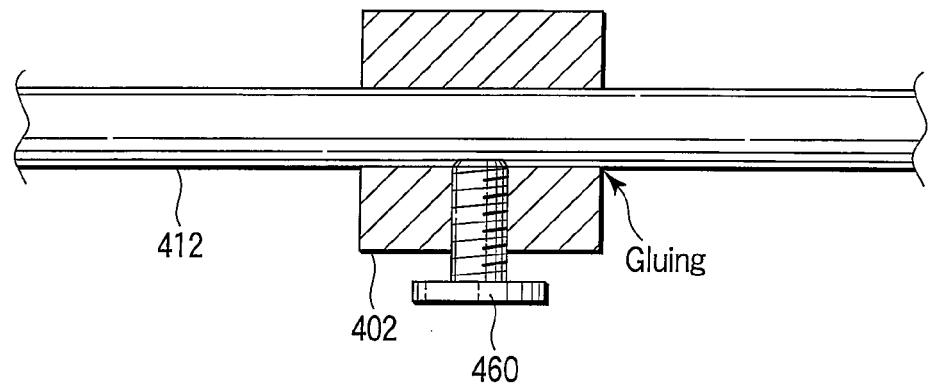
F I G. 10
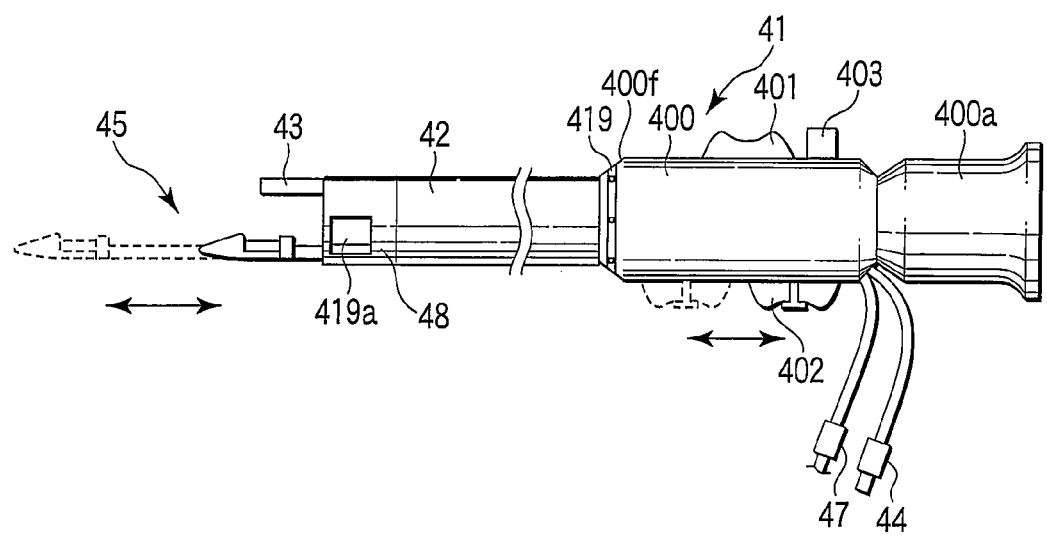
F I G. 11

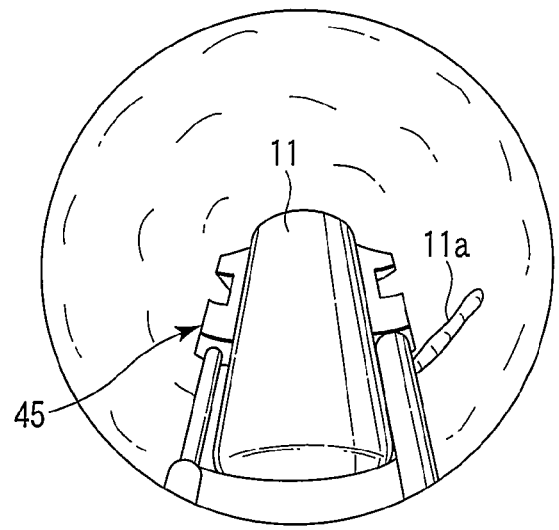
F I G. 12
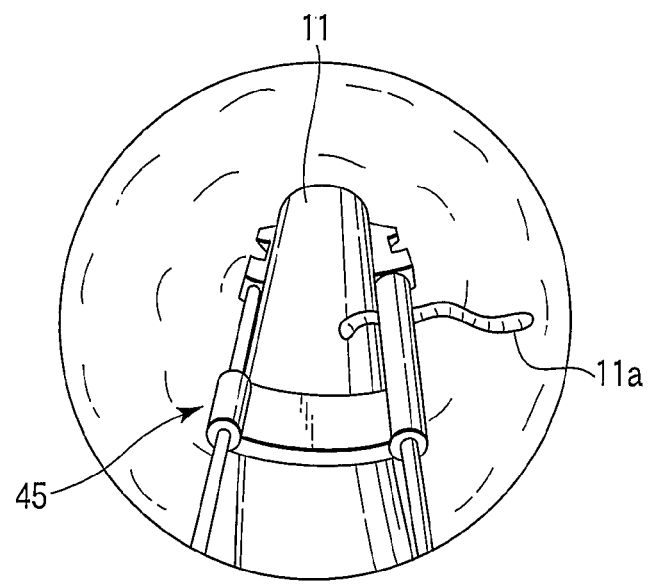
F I G. 13

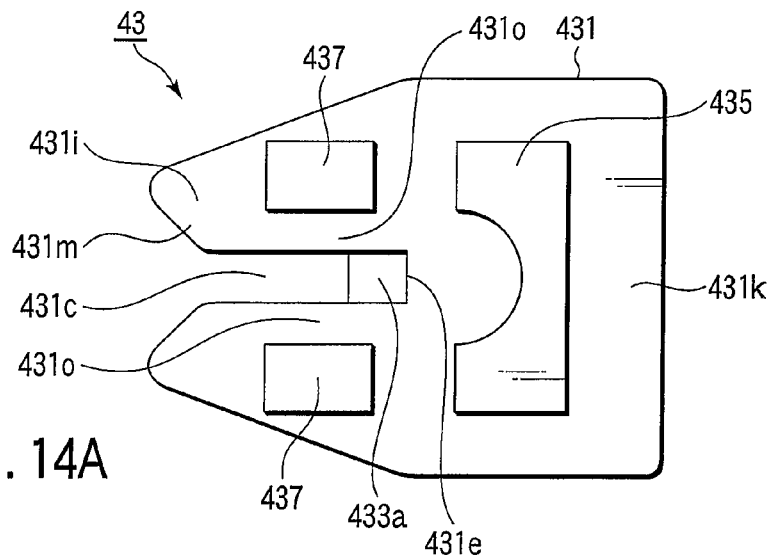
F I G. 14A
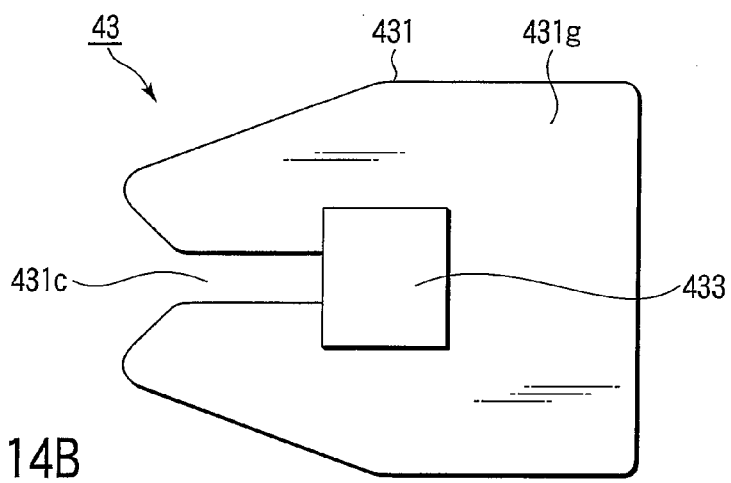
F I G. 14B
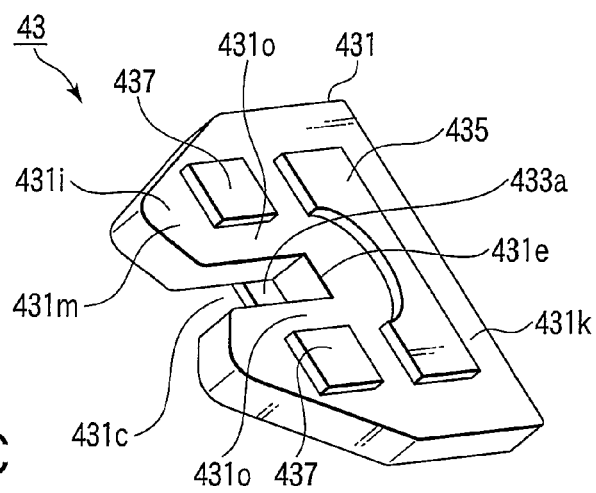
F I G. 14C

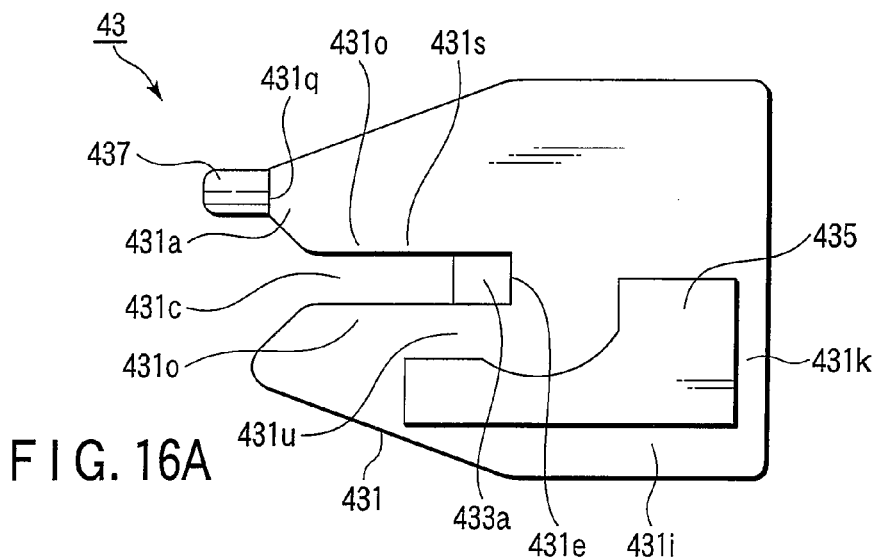
F I G. 16A
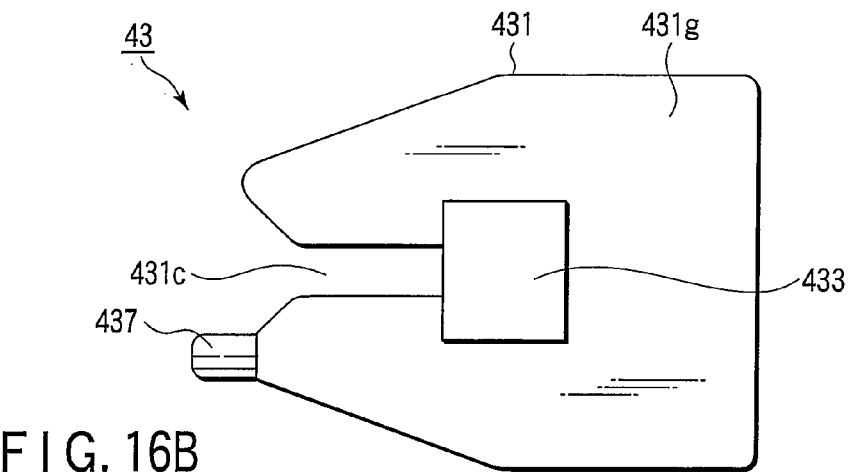
F I G. 16B
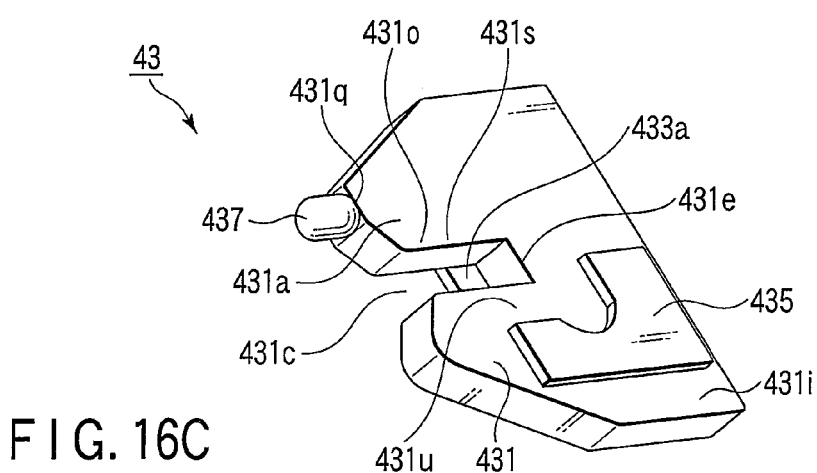
F I G. 16C

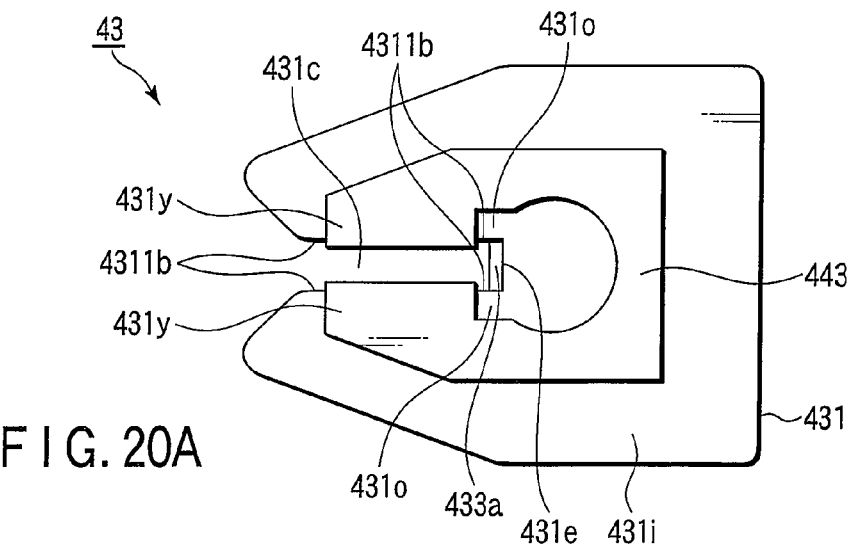
F I G. 20A
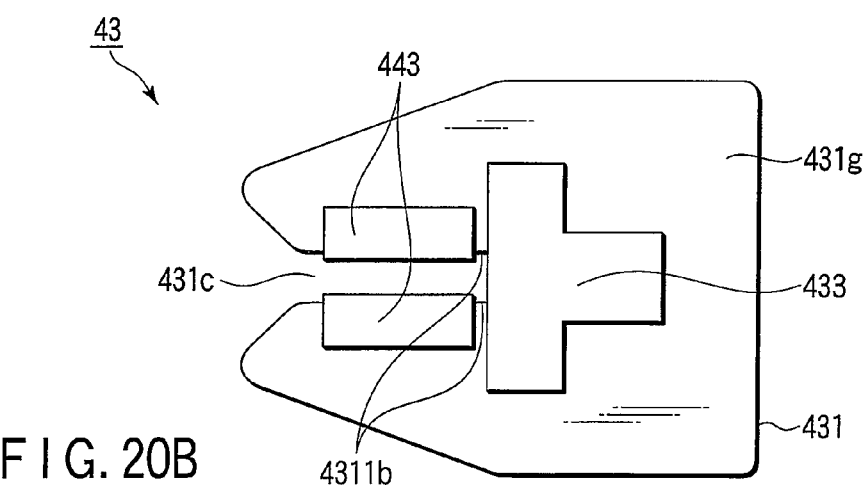
F I G. 20B
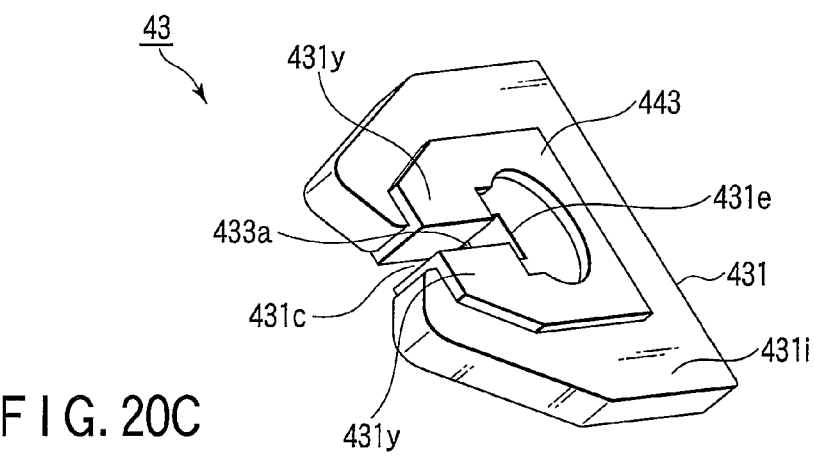
F I G. 20C

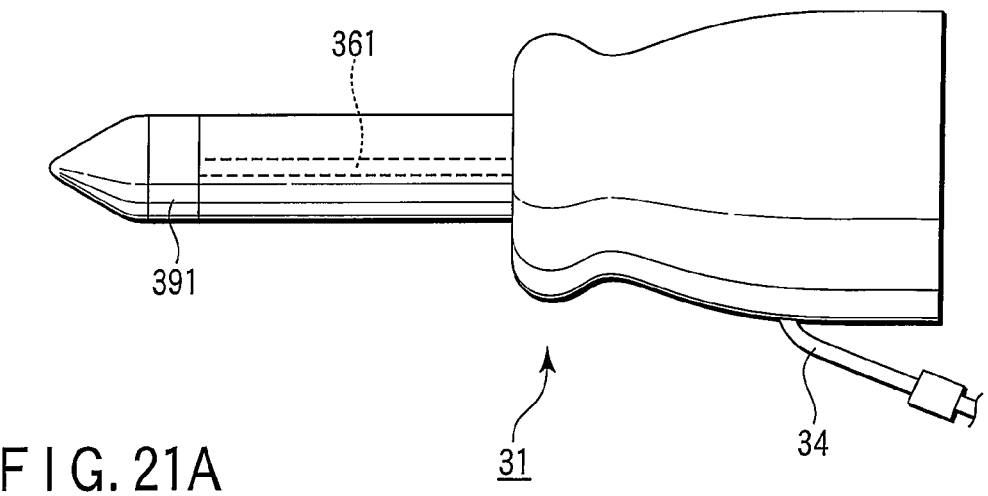
F I G. 21A
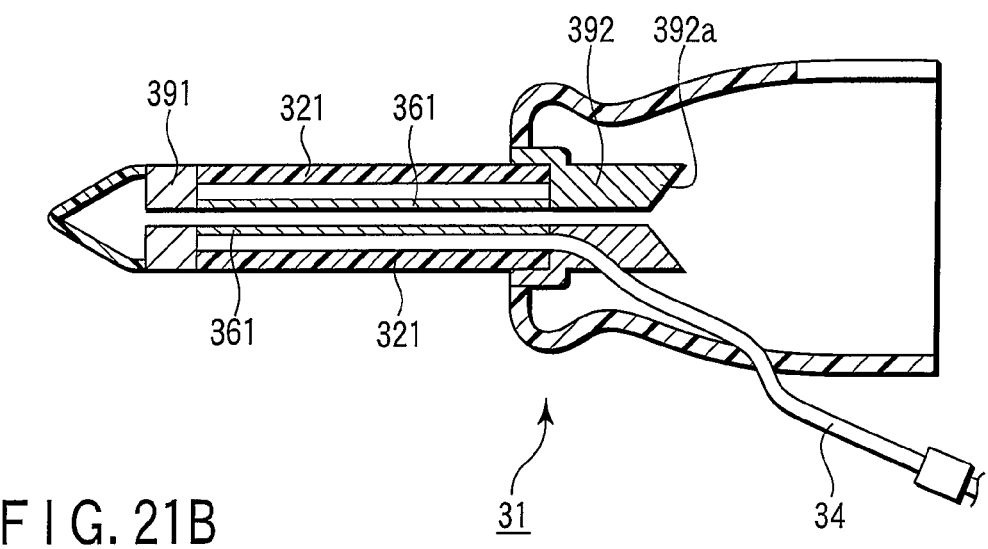
F I G. 21B

ENDOSCOPIC SURGICAL INSTRUMENT

BACKGROUND OF THE INVENTION

1. Field of the Invention

The present invention relates to an endoscopic surgical instrument for treating an object such as a blood vessel.

2. Description of the Related Art

Recently, cardiovascular bypass surgical sometimes uses, as a bypass blood vessel, a lower limb blood vessel such as a great saphenous vein or a upper limb artery such as radial artery of the patient himself/herself. A living tissue harvesting surgical system is used to harvest this blood vessel under endoscopic observation.

This living tissue harvesting surgical system includes an endoscopic surgical instrument which treats an object (living tissue) such as a blood vessel and an endoscope inserted into the endoscopic surgical instrument.

A harvester which is an endoscopic surgical instrument is a tool including a bipolar cutter for electrically cauterizing and cutting branches of a blood vessel.

The tip part of this bipolar cutter is provided with a groove and a pair of electrodes arranged on the upper and lower sides of the groove. When the bipolar cutter moves forward, an electric discharge occurs between the two electrodes to coagulate and cut branches entering the groove while stopping bleeding. The cutter apparatus of the bipolar cutter is made of a ceramic or synthetic resin such as polycarbonate which is a transparent member.

Such surgical apparatuses are disclosed in, for example, Jpn. Pat. Appln. KOKAI Publication Nos. 08-317935, 2003-305054, 2006-326157, and 2006-280662, Jpn. PCT National Publication No. 2000-502585, and Jpn. Pat. Appln. KOKAI Publication Nos. 2000-70280, 2001-61848, and 2005-261945.

Jpn. Pat. Appln. KOKAI Publication No. 08-317935 discloses an electrosurgical method and apparatus which optimize tissue surgical energy efficiency by providing electrodes which can be selected in accordance with the type, thickness, and impedance of a tissue to be engaged or treated by an end-effect device or other parameters.

Jpn. Pat. Appln. KOKAI Publication No. 2003-305054 also discloses an electrosurgical apparatus free from wasteful power consumption.

Jpn. Pat. Appln. KOKAI Publication No. 2006-326157 discloses an endoscopic surgical instrument and endoscopic surgical instrument system which allow one to perform surgical incision and surgical coagulation while quickly and selectively using electrode sections having shapes suitable for the respective surgeries and reduce the load on patients by saving cumbersome operation and shortening the operation time.

Jpn. Pat. Appln. KOKAI Publication No. 2006-280662 discloses an electric surgical instrument which provides a non-slip effect between a living tissue and an incision electrode to facilitate the capture of a living tissue to be incised and can reliably incise only a target region with a high-frequency current.

Jpn. PCT National Publication No. 2000-502585 discloses an apparatus and method for electrosurgery.

Jpn. Pat. Appln. KOKAI Publication No. 2000-70280 discloses a high-frequency surgical instrument which can prevent electrical short circuiting between a pair of grip members and allows reliable coagulation and incision of a tissue.

Jpn. Pat. Appln. KOKAI Publication No. 2001-61848 discloses a high-frequency surgical instrument which is suitable for the incision and excision of an intraoral tissue such as a palatopharyngeal tissue and can safely and reliably coagulate and incise a surgical target tissue without any bleeding.

Jpn. Pat. Appln. KOKAI Publication No. 2005-261945 discloses a biopsy apparatus including a hemostatic electrode which coagulates a living tissue.

BRIEF SUMMARY OF THE INVENTION

There is provided an endoscopic surgical instrument which can satisfactorily coagulate and cut an object.

According to an aspect of the present invention, there is provided an endoscopic surgical instrument comprising an insertion section which is inserted into a body cavity and a surgical section which is disposed on a tip of the insertion section and treated on an object, the surgical section including a body section, and a first electrode, a second electrode, and a third electrode which are disposed on the body section, wherein the surgical section coagulates and cuts the object by using a combination of not less than two of the first electrode, the second electrode, and the third electrode.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a view showing a living tissue harvesting surgical system comprising an endoscopic surgical instrument according to the first embodiment of the present invention;

FIG. 2B is a side view of the harvester;

FIG. 2C is a plan view of the harvester viewed from the bipolar cutter side;

FIG. 6 is a sectional view of the harvester showing its operation and arrangement in the longitudinal direction;

FIG. 10 is a conceptual view of the mounting of a vein keeper lever viewed from an arrow 10 in FIG. 6;

FIG. 11 is a view for explaining the forward/backward movement of the vein keeper lever and vein keeper;

FIG. 12 is a view showing an endoscopic image;

FIG. 13 is a view showing an endoscopic image;

FIG. 14A is a plan view of a portion around a cutter apparatus in the second embodiment;

FIG. 14B is a bottom view of the portion around the cutter apparatus shown in FIG. 14A;

FIG. 14C is a perspective view of the portion around the cutter apparatus shown in FIG. 14A;

FIG. 16A is a plan view of a portion around a cutter apparatus in the fourth embodiment;

FIG. 16B is a bottom view of the portion around the cutter apparatus shown in FIG. 16A;

FIG. 16C is a perspective view of the portion around the cutter apparatus shown in FIG. 16A;

FIG. 20A is a plan view of a portion around a cutter apparatus in the eighth embodiment;

FIG. 20B is a bottom view of the portion around the cutter apparatus shown in FIG. 20A;

FIG. 20C is a perspective view of the portion around the cutter apparatus shown in FIG. 20A;

FIG. 21A is a schematic view of a dissector according to the ninth embodiment; and FIG. 21B is a sectional view of the dissector in the axial direction.

DETAILED DESCRIPTION OF THE INVENTION

Figure 2A:
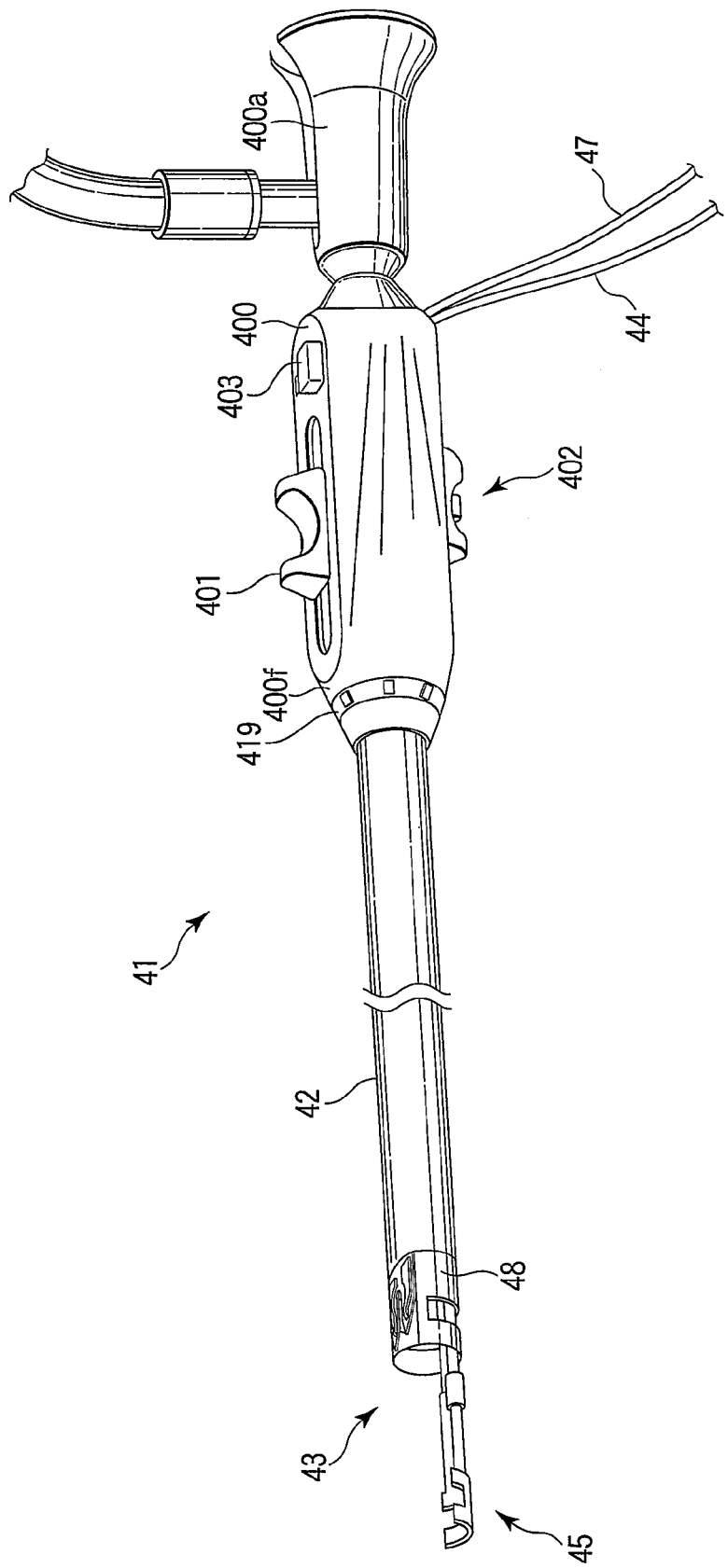
FIG. 2A is a perspective view of a harvester.

The embodiments of the present invention will be described in detail below with reference to the views of the accompanying drawing.

The first embodiment will be described with reference to FIGS. 1 to 13.

Note that in the following embodiments, an object (a living tissue including a tissue to be harvested) is, for example, a blood vessel 11 in a body cavity, an incised branch 11a of a blood vessel, or a bleeding point positioned on a wall portion in a body cavity. In addition, by "surgery" is meant, for example, incision, excision, perforation, exfoliation, coagulation, stopping bleeding, harvesting, cauterization, and cutting.

FIG. 1 shows a living tissue harvesting surgical system (to be simply referred to as a surgical system hereinafter) 101 including an endoscopic surgical instrument (to be described later) according to the first embodiment of the present invention.

For example, cardiac bypass surgery uses a blood vessel as an object for a bypass blood vessel. This blood vessel is, for example, a great saphenous vein (to be also simply referred to as a blood vessel hereinafter) extending from a femoral region in a lower limb to an ankle which is a blood vessel to be harvested and is used for a bypass operation. This blood vessel is, for example, an upper limb artery such as radial artery. This blood vessel is harvested throughout the total length by an endoscopic surgical instrument.

As shown in FIG. 1, the surgical system 101 includes a trocar 21, a dissector 31 as a living tissue exfoliation device, a living tissue cutting tool, i.e., a harvester 41 as an endoscopic surgical instrument, and a rigid endoscope 51 as an endoscope.

The surgical system 101 further includes a television monitor 102 as a display device, a camera processor unit (to be referred to as a CPU hereinafter) 103 connected to the television monitor 102, a television camera cable 104 connected to the CPU 103, a light source device 105 which emits light, a light guide cable 106 connected to the light source device 105, an electro surgical generator device 107, and a gas supply device 108 which supplies a desired gas, e.g., carbon dioxide gas.

Note that the rigid endoscope 51 can extend through the dissector 31 and the harvester 41. The operator harvests a blood vessel while watching the endoscopic image imaged by the rigid endoscope 51 on the television monitor 102.

The rigid endoscope 51 will be described.

A light guide connector part 52 and an eyepiece part 53 are disposed on the base end side of the rigid endoscope 51.

One end of the light guide cable 106 is connected to the light guide connector part 52. The other end of the light guide cable 106 is connected to the light source device 105. A light guide such as a light fiber extends through the light guide cable 106. The light emitted from the light source device 105 is supplied to the rigid endoscope 51 through the light guide cable 106. The rigid endoscope 51 illuminates the object with the light from a tip part 54a of a tip insertion section 54 which is the tip part of the rigid endoscope 51.

The television camera cable 104 is connected to the eyepiece part 53. When the television camera cable 104 is connected to the CPU 103 and the CPU 103 is connected to the television monitor 102, the television monitor 102 displays the image of the object which is imaged by the rigid endoscope 51.

The tip insertion section 54 is disposed on the tip side of the rigid endoscope 51. The tip insertion section 54 is inserted into a rigid endoscope insertion channel 36 (to be described later) of the dissector 31 from the base end side of the dissector 31. The tip insertion section 54 is inserted into the rigid endoscope insertion channel 420 extending through an insertion section 42 (to be described later) of the harvester 41 from the base end side of the harvester 41.

The rigid endoscope 51 includes an observation surface (objective lens) 54b, which is provided for an imaging system (not shown) designed to image an object, at the tip part 54a of the tip insertion section 54. The television monitor 102 displays, via the television camera cable 104 and the CPU 103, the image of the object imaged through the observation surface 54b, as described above.

The dissector 31 will be described next.

An insertion section 32 to be inserted into a body cavity, a gas supply tube 34, and the rigid endoscope insertion channel 36 into which the tip insertion section 54 is inserted are disposed in the dissector 31.

The gas supply tube 34 is connected to a gas supply tubing (not shown) which is connected to the gas supply device 108 to receive a desired gas. This gas is discharged from an opening 35a provided in the tip part of the insertion section 32 of the dissector 31. The rigid endoscope insertion channel 36 extends through the dissector 31 from the base end side of the dissector 31 to the tip part of the insertion section 32 along the axial direction of the dissector 31.

The harvester 41 which is an endoscopic surgical instrument of the present invention will be described next with reference to FIGS. 1 to 13.

The harvester 41 treats an object while the rigid endoscope 51 having the observation surface 54b which is a window part is inserted in the tip part 54a.

As shown in FIGS. 1, 2A, 2B and 2C, the harvester 41 includes the insertion section 42 which is made of a metal and inserted into a body cavity and a grip section 400 which is linked to the base end of the insertion section 42 and allows one to grip the harvester 41.

As shown in FIGS. 2A, 2B and 2C, a base end part 400a of the grip section 400, which is an endoscope holding section, easily and reliably fixes the rigid endoscope 51 to the base end part (base end part 400a) of the harvester 41.

The insertion section 42 will be described next with reference to FIGS. 4 and 5.

A bipolar cutter 43 is disposed on the upper portion of the tip of the insertion section 42. A vein keeper 45, which is a holding member, is disposed inside the lower portion of the tip of the insertion section 42.

Figure 4:
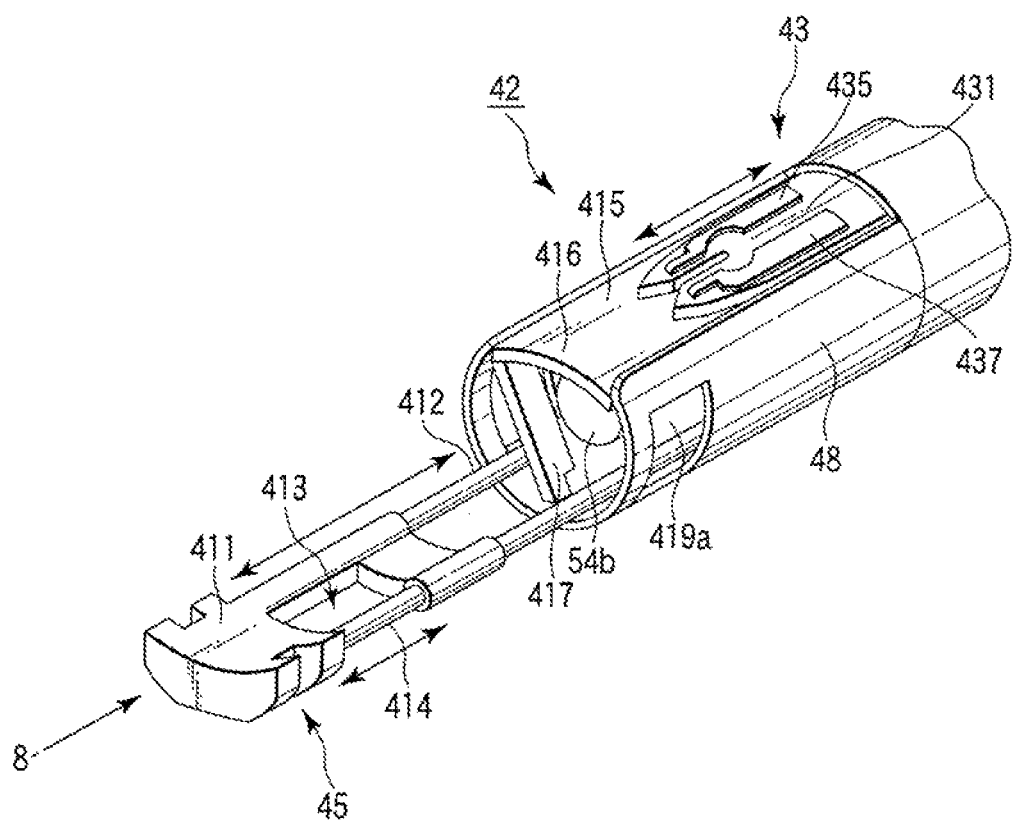
FIG. 4 is a perspective view showing the arrangement of the tip of the harvester (insertion section)
Figure 5:
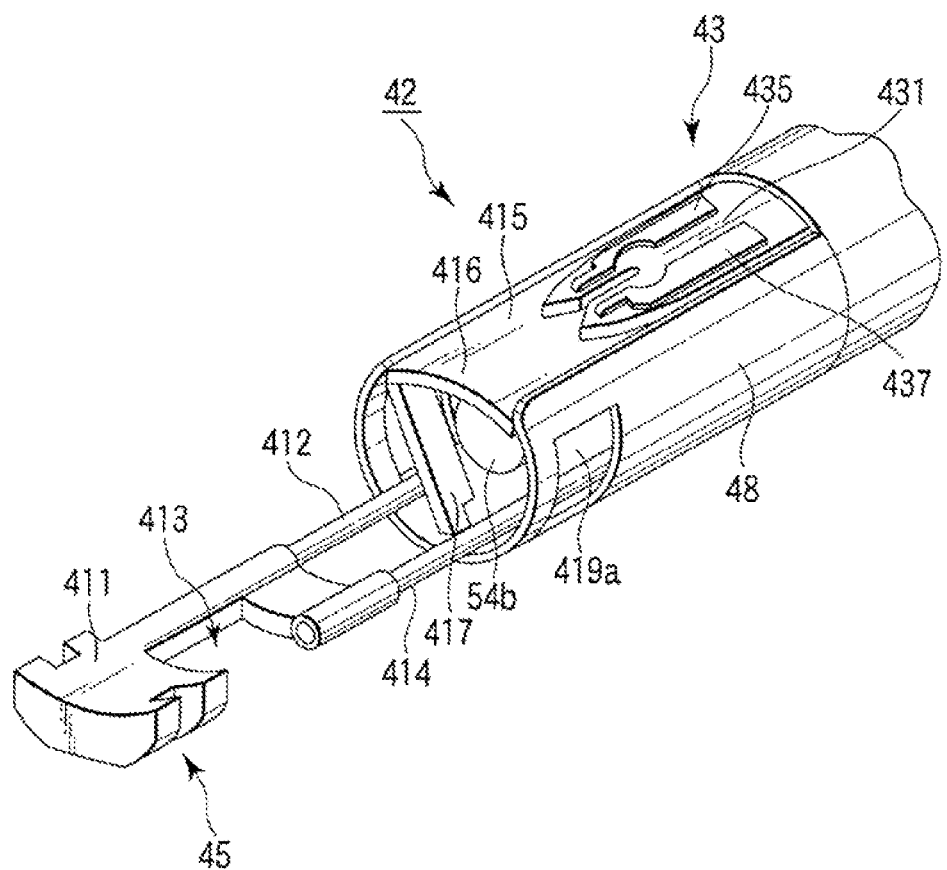
FIG. 5 is a perspective view showing the arrangement of the tip of the harvester (insertion section) and explaining the operation of a lock axis shown in FIG. 4.

As shown in FIGS. 4 and 5, the vein keeper 45 includes a vein keeper axis 412 and a lock axis 414. The vein keeper axis 412 holds an almost U-shaped blood vessel holding base 411 to be movable forward and backward in the longitudinal direction of the insertion section 42. The lock axis 414 is disposed parallel to the vein keeper axis 412 and moves forward and backward in the longitudinal direction of the insertion section 42 relative to the blood vessel holding base 411 to form, in the almost U-shaped blood vessel holding base 411, a closed space 413 which stores a blood vessel. As shown in FIGS. 4 to 6, the vein keeper axis 412 and the lock axis 414 extend through the insertion section 42 and the grip section 400.

As shown in FIG. 4, the lock axis 414 forms the closed space 413 while being locked to the blood vessel holding base 411 like the vein keeper axis 412. Releasing the locked state of the lock axis 414 will open the closed space 413, as shown in FIG. 5. The lock axis 414 then moves forward and backward in the longitudinal direction of the insertion section 42 so as to allow a blood vessel 11 to be stored in the closed space 413.

The bipolar cutter 43 is a surgical section which treats an object.

Figure 7A:
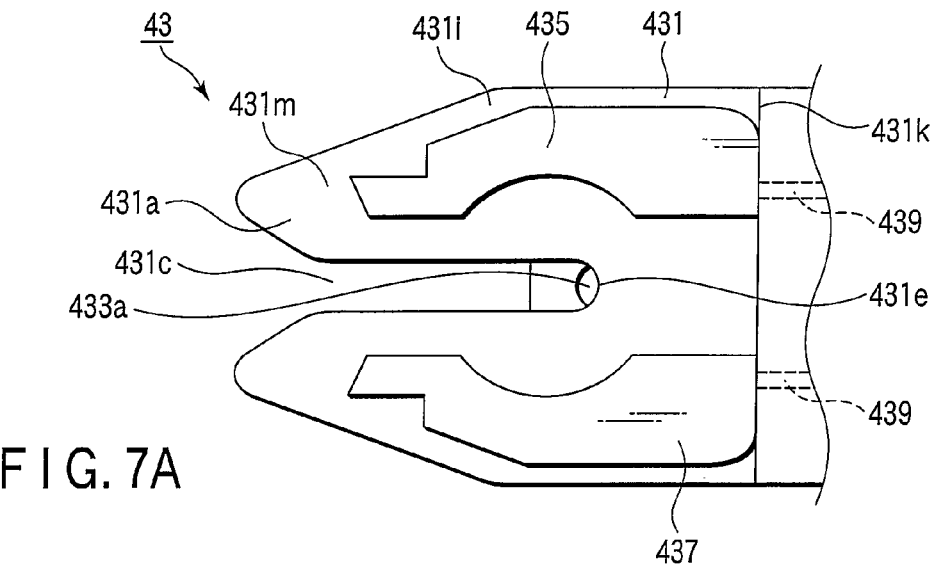
FIG. 7A is a plan view of a portion around a cutter apparatus.
Figure 7B:
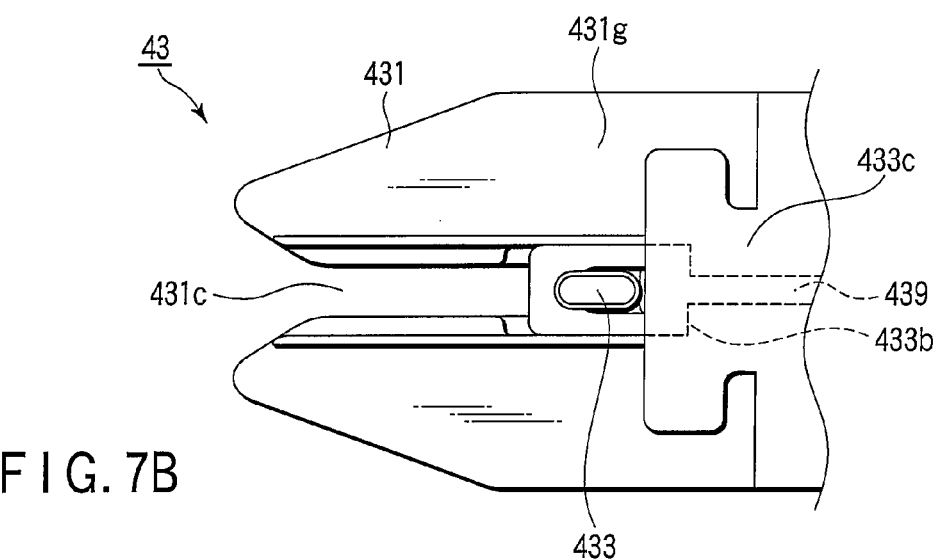
FIG. 7B is a bottom view of the portion around the cutter apparatus shown in FIG. 7A.
Figure 7C:
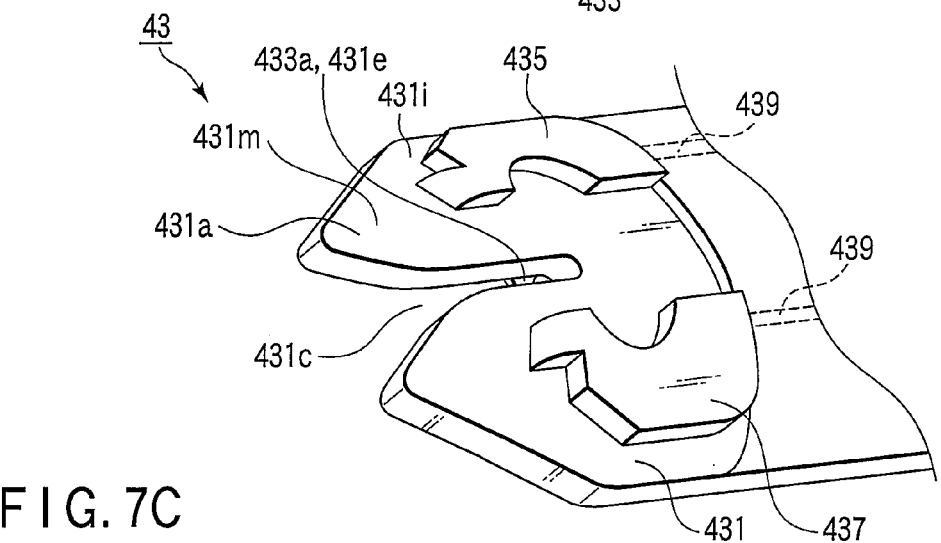
FIG. 7C is a perspective view of the portion around the cutter apparatus shown in FIG. 7A.

As shown in FIGS. 7A, 7B and 7C, the bipolar cutter 43 includes a cutter apparatus 431 as a body section made of a synthetic resin such as polycarbonate which is a transparent insulating member, and a voltage application electrode 433 as the first electrode, a voltage application electrode 435 as the second electrode, and a voltage application electrode 437 as the third electrode which are disposed on the cutter apparatus 431. The cutter apparatus 431 is disposed on the bipolar cutter 43.

The bipolar cutter 43 further includes lead wires 439 which electrically connect the voltage application electrodes 433, 435, and 437 to an electrical cable 47 and supply currents to the voltage application electrodes through the electrical cable 47 so as to make them conductive, and lead wire covers (not shown) which are the covers of the lead wires 439.

The cutter apparatus 431 is also a heat-resistant member. More specifically, the cutter apparatus 431 is made of a high-heat-resistant ceramic structural material, for example, zirconia ceramic (zirconia oxide) or alumina (aluminum oxide).

The cutter apparatus 431 has a V-shaped groove 431c as a guide section which is formed in a tip 431a of the cutter apparatus 431 and guides an object to the voltage application electrode 433 when the cutter apparatus 431 moves toward an object such as the branch 11a.

The voltage application electrode 433 is disposed on an under surface 431g which is the first surface of the cutter apparatus 431 such that a part 433a of the voltage application electrode 433 is exposed from the bottom 431e of the V-shaped groove 431c in the longitudinal direction of the cutter apparatus 431. The area of the part 433a of the voltage application electrode 433 is much smaller than that of the voltage application electrode 435 and that of the voltage application electrode 437.

A current flowing in the voltage application electrode 433 through the lead wire 439 concentrates in the part 433a of the exposed voltage application electrode 433. The part 433a of the voltage application electrode 433 therefore becomes a surgical section at the voltage application electrode 433. An insulating member 433c or the like covers a remaining part 433b of the voltage application electrode 433.

The voltage application electrodes 435 and 437 are disposed on a surface different from the under surface 431g, more specifically, on the same surface. More specifically, the voltage application electrodes 435 and 437 are disposed on an upper surface 431i as the second surface.

The voltage application electrodes 435 and 437 are disposed on the upper surface 431i to extend from a base end 431k to a tip 431m of the upper surface 431i in longitudinal direction of the cutter apparatus 431 so as to be symmetrical with respect to the V-shaped groove 431c in the longitudinal direction of the cutter apparatus 431.

In addition, the voltage application electrodes 433, 435, and 437 are discrete components in this embodiment.

The area of the voltage application electrode 435 is almost equal to that of the voltage application electrode 437.

The part 433a of the voltage application electrode 433, the voltage application electrode 435, and the voltage application electrode 437 incise an object by simultaneously supplying currents to the object.

More specifically, when the part 433a of the voltage application electrode 433, the voltage application electrode 435, and the voltage application electrode 437 are used, since the area of the voltage application electrode 435 is almost equal to that of the voltage application electrode 437, the voltage application electrodes 435 and 437 can be regarded as one voltage application electrode. With this arrangement, the two electrodes, i.e., the voltage application electrode 433 and the electrode constituted by the voltage application electrodes 435 and 437, are provided on the bipolar cutter 43. For this reason, a current from the part 433a of the voltage application electrode 433 into an object differs from a current flowing from the voltage application electrodes 435 and 437 into the object due to the difference between the area of the part 433a of the voltage application electrode 433 and the sum of the areas of the voltage application electrodes 435 and 437. With this difference, the object is incised.

Note that the above description applies to a case in which the voltage application electrodes 433 and 435 are simultaneously used to supply currents to an object and a case in which the voltage application electrodes 433 and 437 are simultaneously used to supply currents to the object.

That is, the bipolar cutter 43 incises an object by using the voltage application electrode 433 and at least one of the voltage application electrodes 435 and 437.

In addition, the voltage application electrodes 435 and 437 simultaneously supply currents into an object to coagulate it. More specifically, since the area of the voltage application electrode 435 is almost equal to that of the voltage application electrode 437, the voltage application electrodes 435 and 437 can be regarded as one electrode, as described above. For this reason, one electrode constituted by the voltage application electrodes 435 and 437 is disposed on the bipolar cutter 43. When the voltage application electrodes 435 and 437 are simultaneously used, since the area of the voltage application electrode 435 is almost equal to that of the voltage application electrode 437, the same quantity of current flows in the object. For this reason, when only the voltage application electrodes 435 and 437 are used, they serve as electrodes for coagulation.

That is, the bipolar cutter 43 coagulates an object by using the voltage application electrodes 435 and 437.

As described above, two or more of the voltage application electrodes 433, 435, and 437 are combined to form electrodes having a plurality of functions, more specifically, electrodes for incision or coagulation.

That is, the bipolar cutter 43 incises or coagulates an object by a combination of two or more of the voltage application electrodes 433, 435, and 437.

As shown in FIGS. 4 and 5, a notched part 415 for receiving the bipolar cutter 43 is formed in the upper surface of the tip side of the insertion section 42. As shown in FIG. 6, a bipolar axis 450 for the forward/backward movement of the bipolar cutter 43 is coupled to the bipolar cutter 43. The bipolar axis 450 is inserted into the insertion section 42 through the notched part 415. A guard part 416 having an arc-shaped cross section is disposed on the inner wall surface of the notched part 415.

As shown in FIGS. 4 to 8, a wiper 417 is disposed on the inner surface of the insertion section 42 on the tip side. The wiper 417 is a wiping section which pivots to wipe off extraneous matter 418 adhering to the observation surface 54b disposed at the tip part 54a of the rigid endoscope 51. As shown in FIG. 6, a wiper axis 500 which is a rod-like axis member coupled to the wiper 417 is disposed in the insertion section 42 so as to extend through it.

While one end of the wiper 417 serves as an axis, the other end of the wiper 417 wipes on the inside of the guard part 416, thereby forming a tip cover 48.

The tip cover 48 is mounted on the insertion section 42 through an internal component (not shown) of the insertion section 42. Using a steel material such as stainless steel for the insertion section 42 can improve the rigidity of the insertion section 42. The tip cover 48 is made of a transparent plastic material (e.g., polycarbonate or polysulfone). Using a plastic material for the tip cover 48 will improve the edge smoothness and the similar portion of the tip part of the insertion section 42. That is, the tip cover 48 can prevent the edge from damaging the inside of a body cavity and improve the property of insertion of the insertion section 42 into a body cavity. In addition, using a transparent member makes it easy to check the extraneous matter 418 when the wiper 417 is operated as the tip cover 48 is clogged with the extraneous matter 418.

As shown in FIGS. 4 and 5, a sweeping hole 419a through which the extraneous matter 418 (see FIG. 8) wiped off by the wiper 417 is swept out is formed in the cylindrical tip cover 48. Note that the extraneous matter 418 includes, for example, blood, fat, and smoke produced by the electro surgical generator device.

Figure 8:
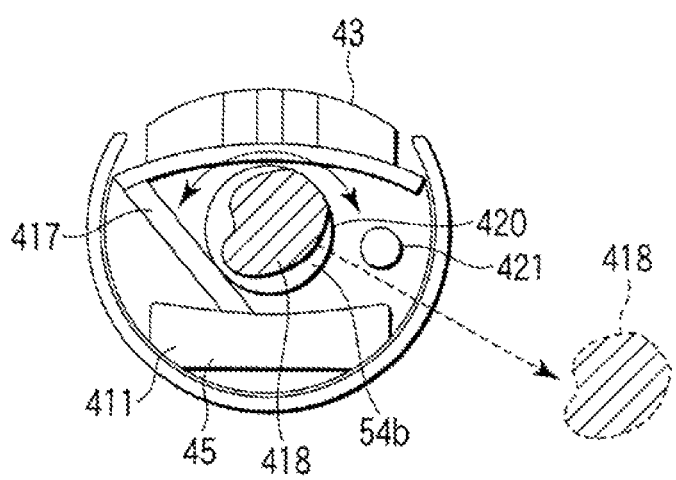
FIG. 8 is a view taken in the direction of an arrow 8 in FIG. 4.

As shown in FIG. 8, an opening of a rigid endoscope insertion channel 420 through which the rigid endoscope 51 extends and an opening of a gas supply channel 421 which supplies a gas are formed adjacent inside the insertion section 42 at a desired position from the tip surface.

The grip section 400 will be described next with reference to FIGS. 1, 2A, 2B, 2C, 6, and 9.

As shown in FIGS. 1 and 2A, 2B, 2C, the electrical cable 47 for the bipolar cutter 43 and a gas supply tube 44 are disposed in the grip section 400.

The electrical cable 47 is connected to the electro surgical generator device 107 through a connector disposed on the base end of the cable 47.

Figure 9:
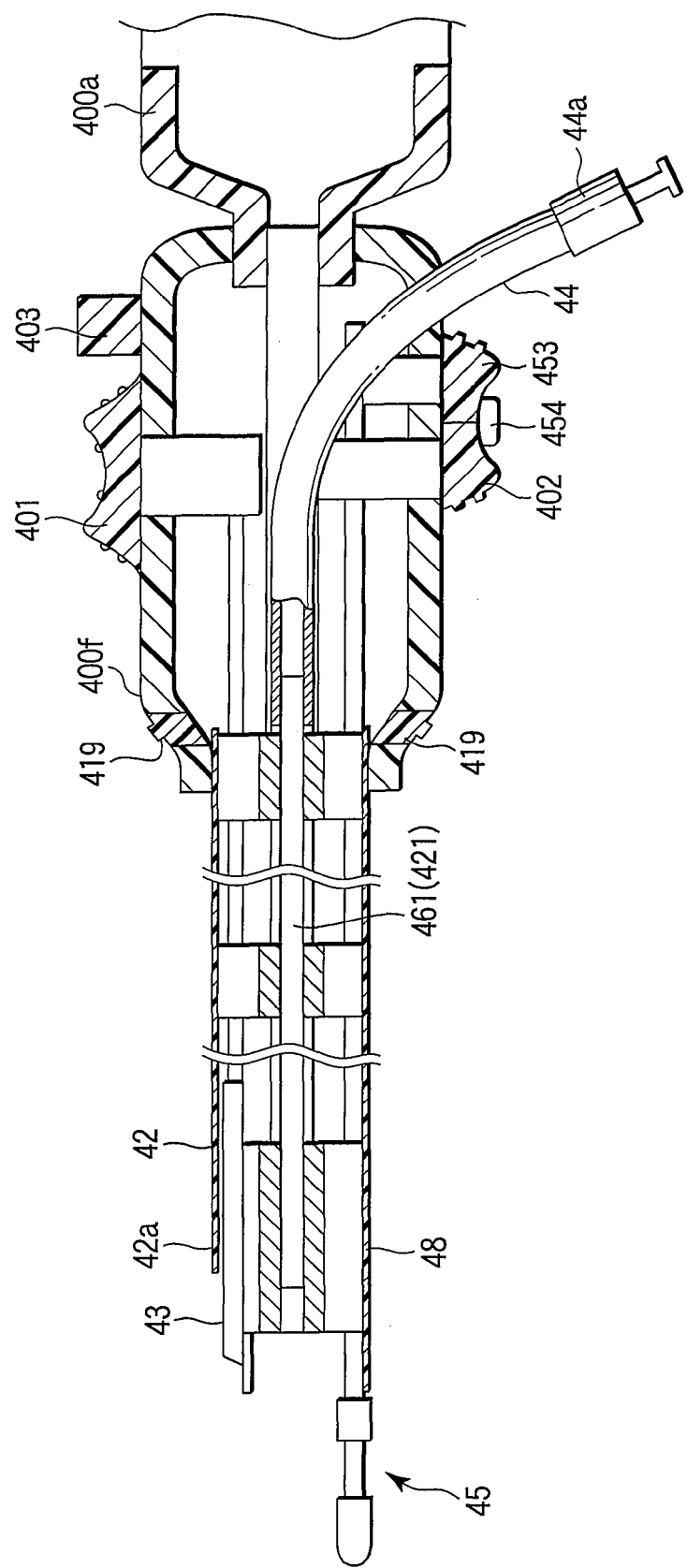
FIG. 9 is a sectional view showing the gas supply arrangement of the harvester in the longitudinal direction.

As shown in FIG. 9, a gas supply connector 44a is disposed on the base end of the gas supply tube 44. The gas supply connector 44a is connected to the gas supply tubing (not shown) which is connected to the gas supply device 108. At this time, the gas supply device 108 supplies a desired gas to the gas supply tube 44 via the gas supply tubing. The desired gas is, for example, carbon dioxide gas, as described above. In the grip section 400, one end of a gas supply tubing 461 is engaged in the gas supply tube 44. As shown in FIG. 9, the gas supply tubing 461 extends through the harvester 41 from the base end side of the grip section 400 to a tip part 42a of the insertion section 42 along the axial direction of the harvester 41. The gas supply tubing 461 is made of a metal which forms the gas supply channel 421. The desired gas supplied from the gas supply device 108 is discharged from the opening of the gas supply channel 421 through the gas supply tube 44 and the gas supply tubing 461.

As shown in FIGS. 1 and 6, a metal tube member 420a made of a metal which forms the rigid endoscope insertion channel 420 extends through the harvester 41 from the base end side of the grip section 400 to the tip part of the insertion section 42 along the axial direction of the harvester 41.

As shown in FIGS. 1, 2A, 2b, 2C, and 6, a bipolar cutter lever 401 which can move forward and backward in the longitudinal direction of the grip section 400 is disposed on the grip section 400 to manipulate the bipolar cutter 43.

As shown in FIG. 6, the bipolar axis 450 which extends through the insertion section 42 and the grip section 400 and is coupled to the bipolar cutter 43 is coupled to the bipolar cutter lever 401. That is, the bipolar cutter 43 is coupled to the bipolar cutter lever 401 through the bipolar axis 450 extending through the insertion section 42.

When the bipolar cutter lever 401 moves forward and backward in the longitudinal direction of the grip section 400, the bipolar cutter 43 moves forward and backward in front of the insertion section 42 through the bipolar axis 450 interlockingly with the forward/backward movement. In other words, when the bipolar cutter lever 401 moves forward and backward along the longitudinal direction of the grip section 400, the forward/backward moving force is transmitted to the bipolar cutter 43 through the bipolar axis 450 to make the bipolar cutter 43 move forward and backward.

As shown FIGS. 1, 2A, 2B, 2C, and 6, a vein keeper lever 402 which can move forward and backward in the longitudinal direction of the grip section 400 is disposed on the grip section 400 to manipulate the vein keeper 45.

As shown in FIG. 6, the vein keeper axis 412 described above which extends through the insertion section 42 and the grip section 400 and is coupled to the vein keeper 45 is coupled to the vein keeper lever 402. That is, the vein keeper 45 is coupled to the vein keeper lever 402 through the vein keeper axis 412 extending through the insertion section 42.

When the vein keeper lever 402 moves forward and backward in the longitudinal direction of the grip section 400, the vein keeper 45 moves forward and backward through the vein keeper axis 412 interlockingly with the forward/backward movement. In other words, when the vein keeper lever 402 moves forward and backward along the longitudinal direction of the grip section 400, the forward/backward moving force is transmitted to the vein keeper 45 through the vein keeper axis 412 to make the vein keeper 45 move forward and backward in front of the insertion section 42.

As shown in FIG. 6, a click assembly 451 which holds the vein keeper lever 402 and the vein keeper axis 412 and fixes their positions is disposed on the inner surface of the grip section 400.

The vein keeper lever 402 and the vein keeper axis 412 integrally move. Interlockingly with this movement, the click assembly 451 moves on the inner surface of the grip section 400. At this time, the click assembly 451 is positioned in, for example, one of three click grooves 452 formed in the inner surface of the grip section 400 to pin-press the inner surface (click groove 452) of the grip section 400. With this operation, at this position, the vein keeper lever 402 and the vein keeper axis 412 are stably fixed by the click assembly 451 which pin-presses the click groove 452.

Note that when force acts on the vein keeper lever 402 in the longitudinal direction, the click assembly 451 easily escapes from the click groove 452.

As shown in FIG. 6, a lock lever 453 and a lock button 454 are disposed on the grip section 400. The lock lever 453 is detachably coupled to the vein keeper lever 402. The lock button 454 is pressed downward to separate the vein keeper lever 402 from the lock lever 453.

The lock lever 453 is coupled to the lock axis 414. When the lock lever 453 moves forward and backward while being separated from the vein keeper lever 402, the lock axis 414 moves forward and backward to allow the blood vessel 11 to be stored in the closed space 413, as shown in FIGS. 4 and 5.

Note that as shown in FIG. 10, the vein keeper lever 402 is firmly fixed to the vein keeper axis 412 with a screw 460 and an adhesive (gluing).

As described above, in this embodiment, as shown in FIG. 11, when the vein keeper lever 402 moves forward and backward, the vein keeper 45 moves forward and backward in front of the insertion section 42. If, therefore, it is difficult to check the state of the branch 11a on an endoscopic image at the time of cutting of the branch 11a shown in FIG. 12, the operator moves the vein keeper lever 402 forward in the longitudinal direction. As shown in FIG. 13, this makes the vein keeper 45 move forward from the tip, thereby allowing the operator to visually recognize an endoscopic image like that shown in FIG. 13 which is suitable for checking the state of the branch 11a.

Figure 3A:
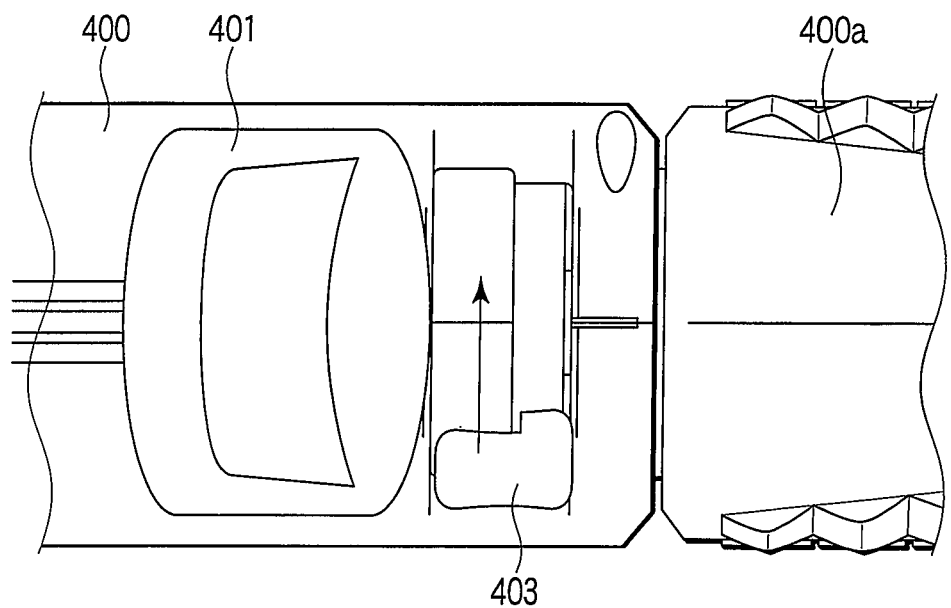
FIG. 3A is an enlarged view of a portion around a switching section.
Figure 3B:
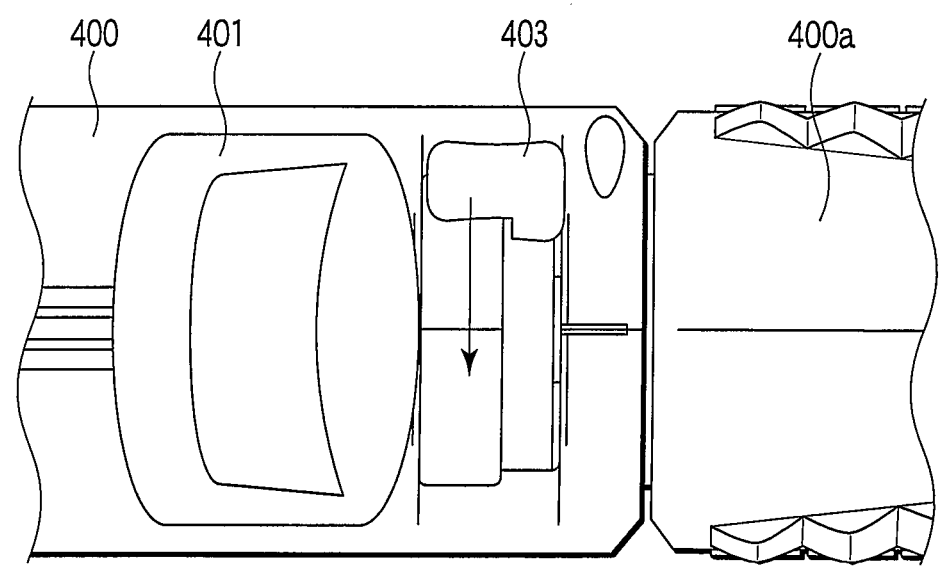
FIG. 3B is an enlarged view of a portion around the switching section pivoted from the state shown in FIG. 3A.

As shown in FIGS. 3A and 3B, a switching section 403 is disposed on the grip section 400. The switching section 403 is a pivot type switch for switching the surgical mode of the bipolar cutter 43 to either the incision mode or the coagulation mode.

Upon switching the surgical mode of the bipolar cutter 43 to the incision mode, the switching section 403 supplies currents to the voltage application electrode 433 and at least one of the voltage application electrodes 435 and 437 through the electrical cable 47 and the lead wires 439.

Upon switching the surgical mode of the bipolar cutter 43 to the coagulation mode, the switching section 403 supplies currents to the voltage application electrodes 435 and 437 through the electrical cable 47 and the lead wires 439.

The switching section 403 is disposed closer to the base end part 400a than the bipolar cutter lever 401.

In addition, the switching section 403 is biased by a spring (not shown) so as to stay at the position in FIG. 3A. In this state, in general, the switching section 403 is switched to the position for incision. In order to switch the switching section 403 to the position for coagulation, the switching section 403 is pivoted to the position shown in FIG. 3B against the spring force. Note that when the operator releases his/her fingers that hold the switching section 403 at the position shown in FIG. 3B, the switching section 403 restores (returns) to the position shown in FIG, 3A with the spring force.

As shown in FIGS. 2A, 2b, 2C and 6, a wiper lever 419 as a manipulation section is disposed on the grip section 400 throughout the entire circumference of a tip 400f of the grip section 400 in the circumferential direction relative to the longitudinal direction of the grip section 400 so as to be coupled to the wiper axis 500 and to manipulate the wiper 417 through the wiper axis 500.

An operation method in this embodiment will be described next.

This embodiment will exemplify a case in which both the voltage application electrode 435 and the voltage application electrode 437 are used.

The switching section 403 pivots to switch the surgical mode of the bipolar cutter 43 to the incision mode. This will supply currents to the voltage application electrodes 433, 435, and 437 through the electro surgical generator device 107, the electrical cable 47, and the lead wires 439.

Since the area of the voltage application electrode 435 is almost equal to that of the voltage application electrode 437, the voltage application electrodes 435 and 437 can be regarded as one electrode. Therefore, the two electrodes, i.e., the voltage application electrode 433 and the electrode constituted by the voltage application electrodes 435 and 437, are disposed on the bipolar cutter 43.

An object is therefore incised by a current flowing from part of the voltage application electrode 433 and currents flowing from the voltage application electrodes 435 and 437.

Note that the object is incised in the same manner when the voltage application electrodes 433 and 435 are used and when the voltage application electrodes 433 and 437 are used.

The switching section 403 pivots to switch the surgical mode of the bipolar cutter 43 to the coagulation mode. With this operation, currents flow in the voltage application electrodes 435 and 437 through the electro surgical generator device 107, the electrical cable 47, and the lead wires 439.

Since the area of the voltage application electrode 435 is almost equal to that of the voltage application electrode 437, one electrode constituted by the voltage application electrodes 435 and 437 is disposed on the bipolar cutter 43.

The object is therefore coagulated by currents flowing from the voltage application electrodes 435 and 437.

As described above, this embodiment can satisfactorily coagulate and cut an object by using at least two of the voltage application electrodes 433, 435, and 437 in either incision mode or coagulation mode. Noteworthy that in incision mode, the living tissue is both cauterized and cut while in coagulation mode only hemostasis is provided.

In addition, this embodiment can coagulate and cut an object with one endoscopic surgical instrument without selectively using an endoscopic surgical instrument for incision and an endoscopic surgical instrument for coagulation.

In addition, the embodiment need not switch endoscopic surgical instruments for incision and coagulation, and hence can shorten the surgical time.

In this embodiment, the voltage application electrodes 433, 435, and 437 are disposed on the bipolar cutter 43 disposed on the tip part 42a of the insertion section 42. The embodiment can therefore satisfactorily incise and coagulate an object even in a narrow body cavity.

In addition, in this embodiment, it is possible to coagulate a necessary region to a necessary degree by using the voltage application electrodes 435 and 437 each having an area larger than that of part of the voltage application electrode 433.

Furthermore, this embodiment selectively performs incision and coagulation using the difference in area between part of the voltage application electrode 433 and each of the voltage application electrodes 435 and 437, and hence can coagulate and cut an object without changing output modes (current values).

The second embodiment of the present invention will be described next with reference to FIGS. 14A, 14B, and 14C. Note that the same reference numerals as in the first embodiment described above denote the same constituent elements as those in the first embodiment, and a repetitive description will be omitted.

Voltage application electrodes 437 in this embodiment are disposed on two sides 431o of a V-shaped groove 431c on an upper surface 431i so as to be closer to a tip 431m of a cutter apparatus 431 than a part 433a of a voltage application electrode 433 in the longitudinal direction of the cutter apparatus 431.

On the upper surface 431i, a voltage application electrode 435 is disposed closer to a base end 431k of the cutter apparatus 431 than the voltage application electrode 433 and a bottom 431e of the V-shaped groove 431c so as to be disposed on the same straight lines as those of the voltage application electrodes 437 in the longitudinal direction of the cutter apparatus 431.

In this manner, the voltage application electrode 435 and the voltage application electrodes 437 are positioned on the upper surface 431i so as to be vertically symmetrical with respect to part 433a of the voltage application electrode 433 in the longitudinal direction of the cutter apparatus 431.

This arrangement in this embodiment can press, the right or left area of the upper surface 431i against an object and satisfactorily coagulate and cut the object by using the voltage application electrodes 435 and 437.

Figure 15A:
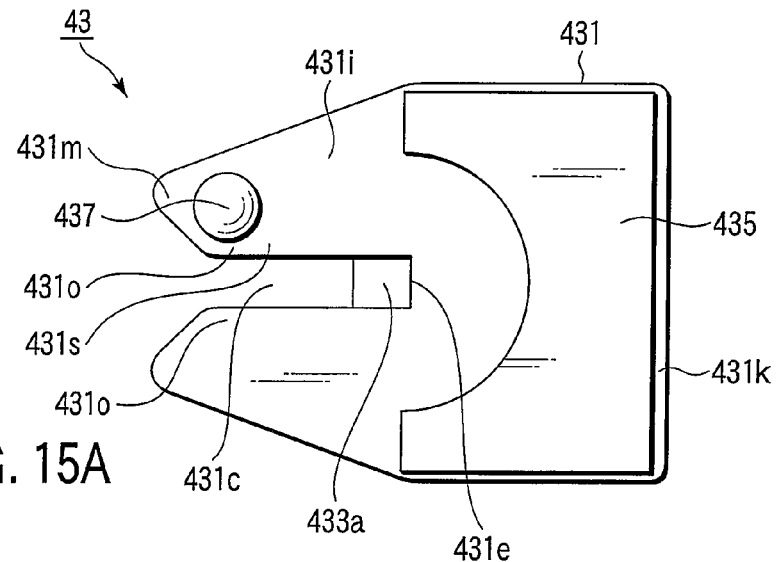
FIG. 15A is a plan view of a portion around a cutter apparatus in the third embodiment.
Figure 15B:
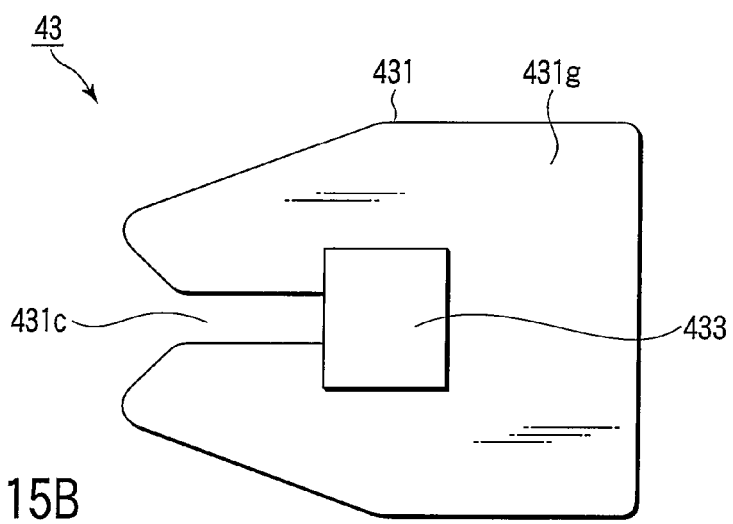
FIG. 15B is a bottom view of the portion around the cutter apparatus shown in FIG. 15A.
Figure 15C:
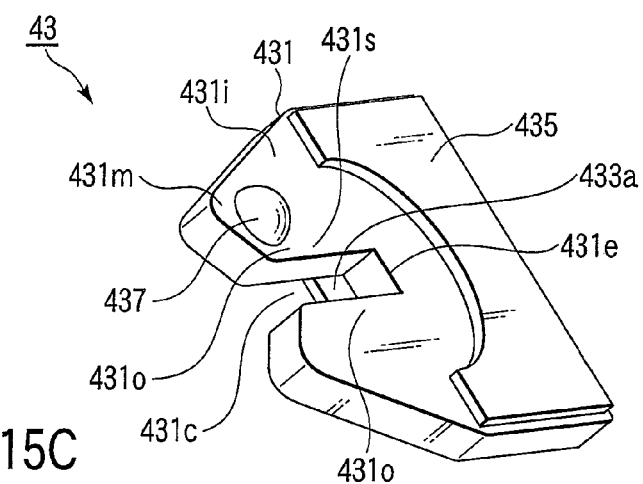
FIG. 15C is a perspective view of the portion around the cutter apparatus shown in FIG. 15A.

The third embodiment of the present invention will be described next with reference to FIGS. 15A, 15B, and 15C. Note that the same reference numerals as in the first embodiment described above denote the same constituent elements as those in the first embodiment, and a repetitive description will be omitted.

A voltage application electrode 435 in this embodiment is disposed on an entire upper surface 431i from a bottom 431e of a V-shaped groove 431c to a base end 431k.

A voltage application electrode 437 is disposed on one side 431s of two sides 431o of the V-shaped groove 431c so as to be located on a tip 431m side of a cutter apparatus 431 and protrude from the upper surface 431i. The voltage application electrode 437 is a convex part protruding from the upper surface 431i.

More specifically, the voltage application electrode 437 is disposed on, for example, the right side of the V-shaped groove 431c on the tip 431m side of the cutter apparatus 431 so as to protrude from the upper surface 431i.

As described above, in this embodiment, since the voltage application electrode 437 is disposed to protrude from the upper surface 431i, it is possible to coagulate and cut an object at a pinpoint.

Note that voltage application electrode 437 may be disposed on the left side of the V-shaped groove 431c.

The fourth embodiment of the present invention will be described next with reference to FIGS. 16A, 16B, and 16C. Note that the same reference numerals as in the first embodiment described above denote the same constituent elements as those in the first embodiment, and a repetitive description will be omitted.

A voltage application electrode 435 is disposed on an upper surface 431i.

A voltage application electrode 437 is disposed on a side surface 431q which is the third surface different from an under surface 431g and the upper surface 431i.

More specifically, the voltage application electrode 435 in this embodiment is disposed on the upper surface 431i so as to have an almost L shape surrounding a remaining side 431u and bottom 431e of a V-shaped groove 431c.

In addition, the voltage application electrode 437 in this embodiment is disposed on the side surface 431q so as to protrude from a tip 431a of a cutter apparatus 431 which is located on one side 431s of the V-shaped groove 431c. The voltage application electrode 437 is a convex part protruding from the tip 431a.

More specifically, the voltage application electrode 435 in this embodiment is disposed on the left side of the V-shaped groove 431c on the upper surface 431i so as to be positioned between a part 433a of a voltage application electrode 433 and a base end 431k along the longitudinal direction of the cutter apparatus 431. The voltage application electrode 437 in the embodiment is disposed on the right side of the V-shaped groove 431c so as to protrude from the tip 431a of the cutter apparatus 431.

As described above, in this embodiment, since the voltage application electrode 437 protrudes from the tip 431a, it is also possible to satisfactorily coagulate and cut an object by moving the cutter apparatus 431 forward toward the object without pressing the cutter apparatus against the object.

Note that the voltage application electrode 435 and the voltage application electrode 437 may be disposed to be symmetrical with respect to the V-shaped groove 431c.

Figure 17A:
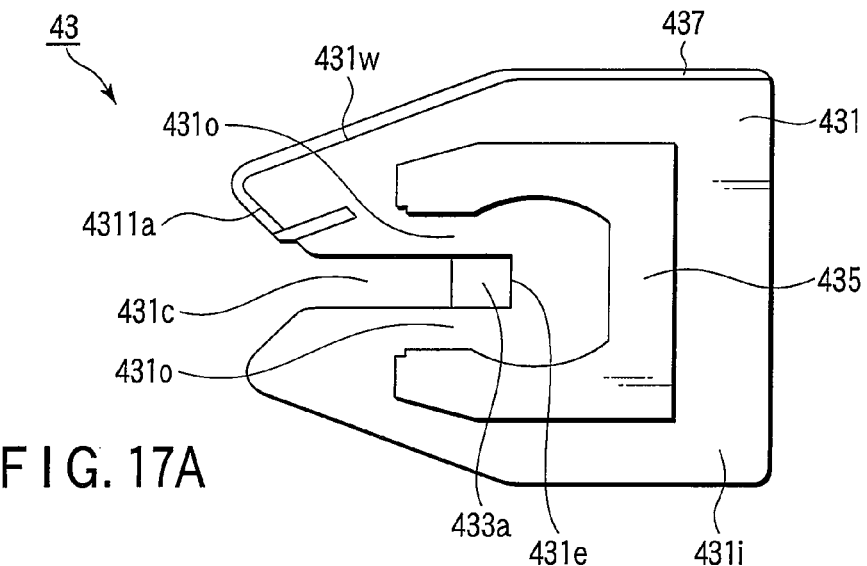
FIG. 17A is a plan view of a portion around a cutter apparatus in the fifth embodiment.
Figure 17B:
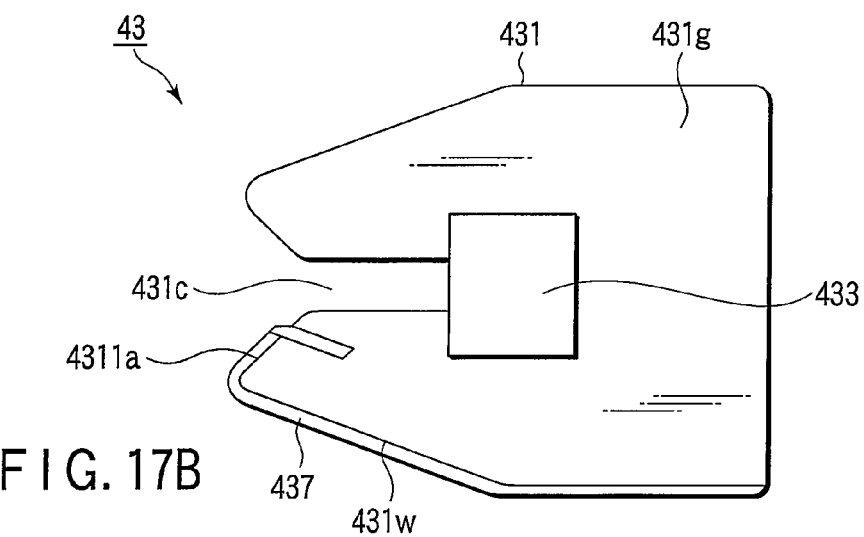
FIG. 17B is a bottom view of the portion around the cutter apparatus shown in FIG. 17A.
Figure 17C:
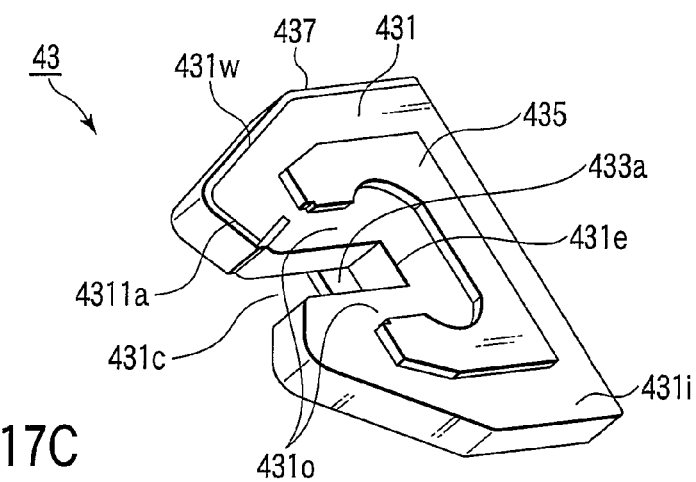
FIG. 17C is a perspective view of the portion around the cutter apparatus shown in FIG. 17A.

The fifth embodiment of the present invention will be described with reference to FIGS. 17A, 17B, and 17C. Note that the same reference numerals as in the first embodiment described above denote the same constituent elements as those in the first embodiment, and a repetitive description will be omitted.

A voltage application electrode 435 in this embodiment is disposed on an upper surface 431i so as to have an almost U shape surrounding two sides 431o and bottom 431e of a V-shaped groove 431c. That is, the voltage application electrode 435 is disposed on the upper surface 431i so as to surround the V-shaped groove 431c.

A voltage application electrode 437 is disposed in continuous contact with one side surface 431w of the cutter apparatus 431 and a side surface 4311a on the tip side of the V-shaped groove 431c which is in continuous contact with the side surface 431w.

In this embodiment, this arrangement makes it possible to secure a large area for coagulation. In the embodiment, this can shorten the surgical time for coagulation.

Figure 18A:
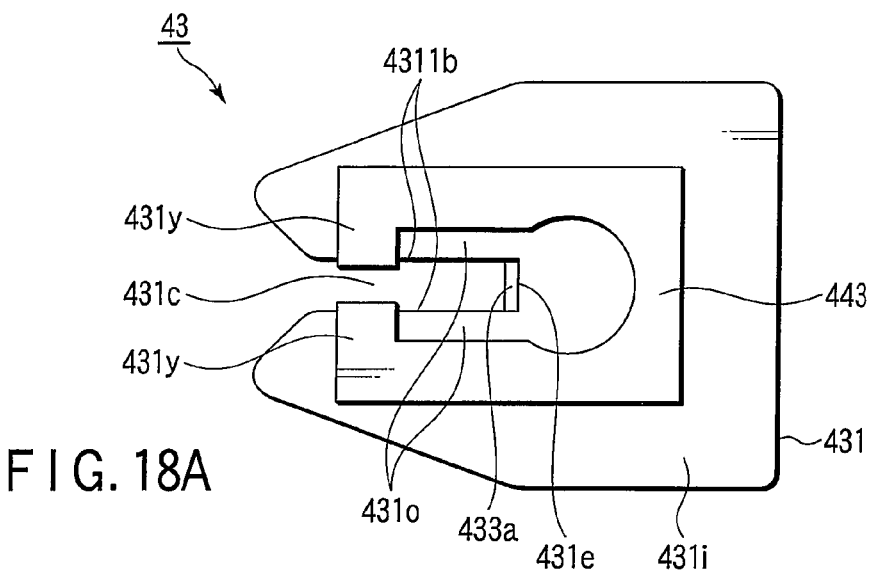
FIG. 18A is a plan view of a portion around a cutter apparatus in the sixth embodiment.
Figure 18B:
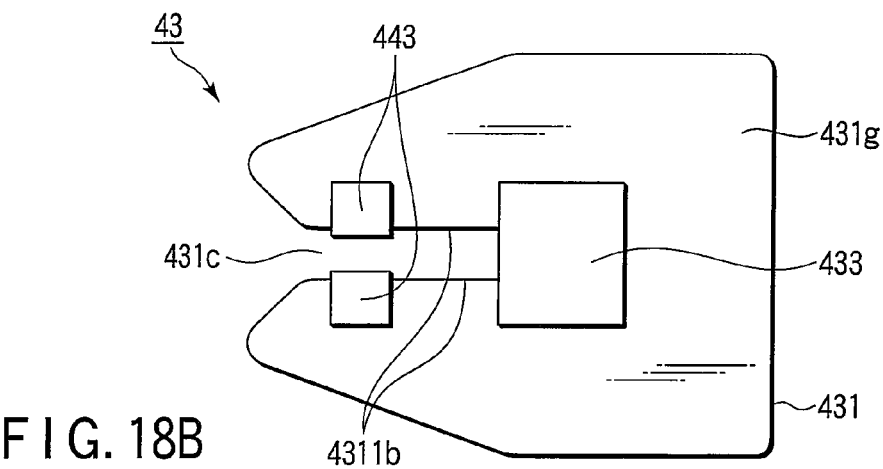
FIG. 18B is a bottom view of the portion around the cutter apparatus shown in FIG. 18A.
Figure 18C:
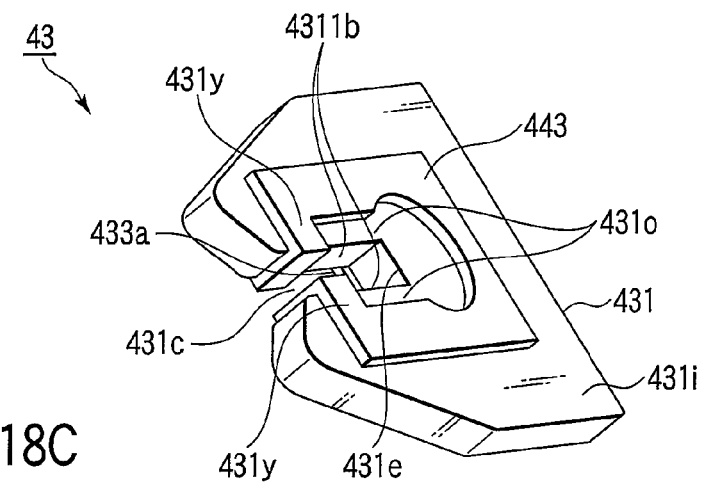
FIG. 18C is a perspective view of the portion around the cutter apparatus shown in FIG. 18A.

The sixth embodiment of the present invention will be described next with reference to FIGS. 18A, 18B, and 18C. Note that the same reference numerals as in the first embodiment described above denote the same constituent elements as those in the first embodiment, and a repetitive description will be omitted.

Voltage application electrodes 435 and 437 in this embodiment are integrated into a voltage application electrode 443 as an integral electrode. That is, this arrangement includes two electrodes, i.e., a voltage application electrode 433 and the voltage application electrode 443, and hence a switching section 403 is omitted.

The voltage application electrode 443 is disposed on an upper surface 431i so as to have an almost U shape surrounding two sides 431o and bottom 431e of a V-shaped groove 431c. The voltage application electrode 443 is also bent from U-shaped tips 431y toward inner surfaces 4311b of the V-shaped groove 431c to be disposed on the inner surfaces 4311b, and is further bent from the inner surfaces 4311b to be disposed on an under surface 431g. In this manner, the voltage application electrode 443 is in tight contact with the inside of a cutter apparatus 431.

In incision mode, the voltage application electrode 433 and the voltage application electrode 443 supply current to an object. In coagulation mode, the voltage application electrode 443 on the upper surface 431i supplies a current to the object. At this time, even if a current flows in the voltage application electrode 433, since only the upper surface 431i comes into contact with the object, the object is not incised.

As described above, this embodiment uses the two electrodes, i.e., the voltage application electrode 433 and the voltage application electrode 443, and hence supplies current to both the voltage application electrode 433 and the voltage application electrode 443 in both the surgical modes, i.e., the coagulation mode and the incision mode. This makes it unnecessary to switch currents, and hence the arrangement need not use the switching section 403. The embodiment can therefore achieve a cost reduction.

Figure 19A:
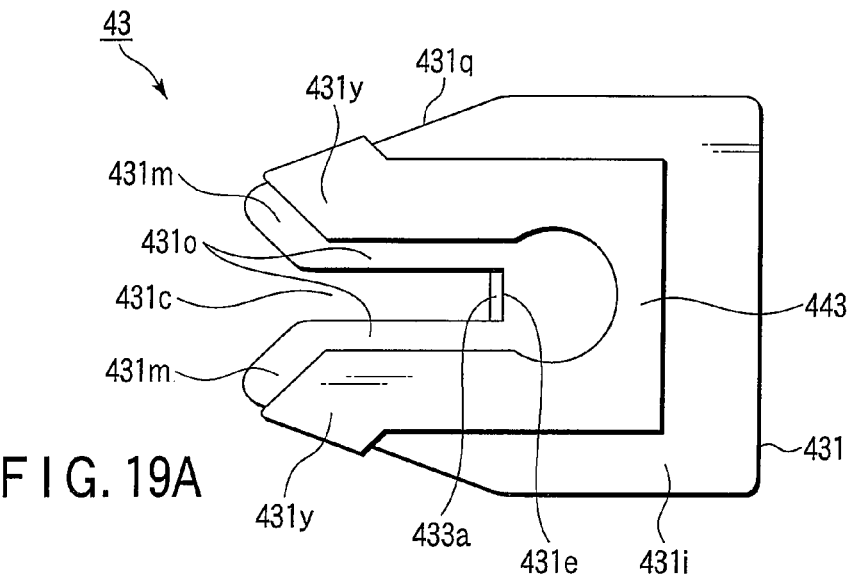
FIG. 19A is a plan view of a portion around a cutter apparatus in the seventh embodiment.
Figure 19B:
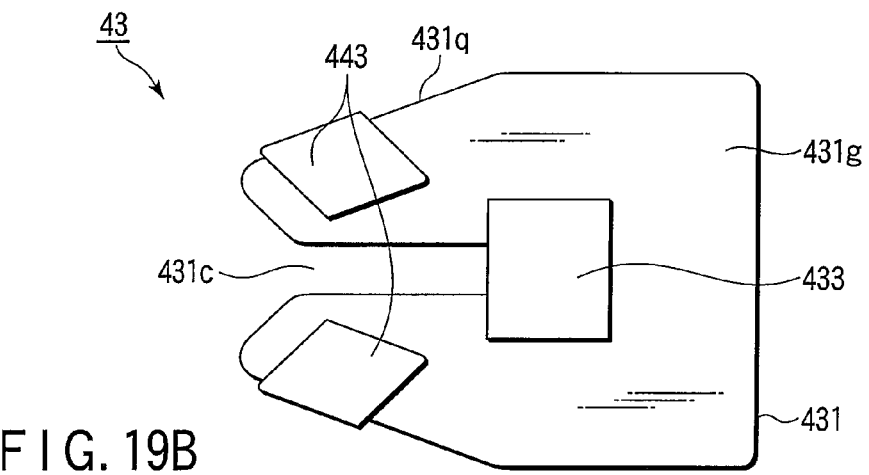
FIG. 19B is a bottom view of the portion around the cutter apparatus shown in FIG. 19A.
Figure 19C:
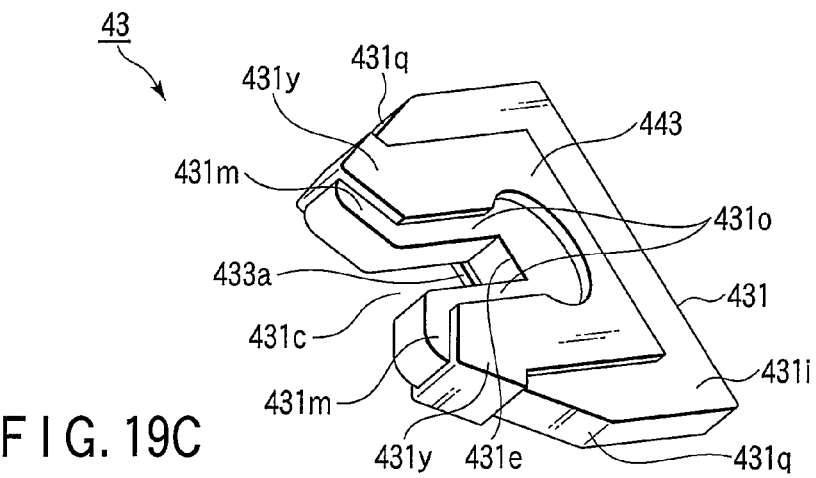
FIG. 19C is a perspective view of the portion around the cutter apparatus shown in FIG. 19A.

The seventh embodiment of the present invention will be described next with reference to FIGS. 19A, 19B, and 19C. Note that the same reference numerals as in the first and sixth embodiments described above denote the same constituent elements as those in the first embodiment, and a repetitive description will be omitted.

A voltage application electrode 443 is disposed on an upper surface 431i so as to have an almost U shape surrounding two sides 431o and bottom 431e of a V-shaped groove 431c. The voltage application electrode 443 is bent from a tip 431m on which a U-shaped tip 431y is disposed toward a side surface 431q to be disposed on the side surface 431q, and is further bent from the side surface 431q to be disposed on an under surface 431g. In this manner, the voltage application electrode 443 is disposed to be hooked on side surfaces 431q of a cutter apparatus 431.

With this arrangement, this embodiment can obtain the same effect as that of the sixth embodiment.

The eighth embodiment of the present invention will be described next with reference to FIGS. 20A, 20B, and 20C. Note that the same reference numerals as in the first and sixth embodiments described above denote the same constituent elements as those in the first embodiment, and a repetitive description will be omitted.

A voltage application electrode 443 is disposed in the same manner as in the sixth embodiment.

The voltage application electrode 433 is disposed in a T shape.

In this case, a cutter apparatus 431 has elastic force.

In this embodiment, this makes it possible to press a cutter apparatus 431 with elastic force against an object and satisfactorily incise and coagulate the object even if the object is rigid.

The ninth embodiment of the present invention will be described next with reference to FIGS. 21A and 21B. Note that the same reference numerals as in the first embodiment described above denote the same constituent elements as those in the first embodiment, and a repetitive description will be omitted.

FIG. 21A is a schematic view of a dissector 31 in this embodiment. FIG. 21B is a sectional view of the dissector 31 in the axial direction.

An insertion section 321 is formed as a tube.

The insertion section 321 includes a tip part 391, a base end part 392 disposed closer to the base end side than the tip part 391, and a scope tube 361 sandwiched between the tip part 391 and the base end part 392 so as to be located in the middle part between the tip part 391 and the base end part 392.

The insertion section 321 is made of a material that can reduce the insertion resistance at the time of insertion into a body cavity, e.g., PTFE (polytetrafluoroethylene), FEP (fluorinated ethylene propylene), or ETFE (ethylene tetrafluoroethylene).

The tip part 391 and the base end part 392 are, for example, plastic parts. The scope tube 361 is a tube made of a metal, e.g., stainless steel. The scope tube 361 is disposed in the insertion section 321.

Threads (not shown) are formed on the two end parts of the scope tube 361. The tip part 391 and the base end part 392 are fixed to the scope tube 361 with the threads. That is, the scope tube 361 sandwiched between the tip part 391 and the base end part 392 is fixed to the tip part 391 and the base end part 392 with the threads, thereby fixing the insertion section 321 in which the scope tube 361 is disposed.

With this arrangement, this embodiment can easily fix the tip part 391 and the base end part 392 even if the insertion section 321 is made of a material with a poor adhesive property such as PTFE.

An end surface 392a of the base end part 392 is tapered. In this embodiment, this makes it possible to smoothly insert a tip part 54a of a rigid endoscope 51 into the dissector 31 when inserting the rigid endoscope 51 into an insertion section 32.

Note that the present invention is not limited to the above embodiments, and constituent elements can be variously modified and embodied at the execution stage within the spirit and scope of the invention. Various inventions can be formed by proper combinations of a plurality of constituent elements disclosed in the above embodiments.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscopic surgical instrument comprising:
   an insertion section configured to be inserted into a body cavity and comprising a tip end part, a base end part, and a central axis extending from the tip end part to the base end part in a longitudinal direction of the insertion section;
   a vein keeper arranged at the tip end part of the insertion section and configured to hold a blood vessel to be harvested;

a surgical section arranged at the tip end part of the insertion section at a position shifted from the central axis in a radial direction of the insertion section and configured to cut off a side branch from between the blood vessel to be harvested and a wall portion in the body cavity;

a first electrode disposed on a first surface of the surgical section that faces the vein keeper side;

a second electrode and a third electrode which are disposed on a second surface of the surgical section, the second surface being an opposite surface to that of the first surface; and a switching section configured to switch to one of an incision mode in which the side branch is cut off by supplying a current to the first electrode and the second electrode from an electric energy supply source and a coagulation mode in which the wall portion in the body cavity is coagulated by supplying a current to the second electrode and the third electrode from the electric energy supply source.

2. The instrument according to claim 1, wherein an exposed area of the first electrode is smaller than each of the area of the second electrode and of the third electrode.

3. The instrument according to claim 2, wherein
the surgical section includes a V-shaped groove which is formed in a tip end of the surgical section and serves as a guiding section which guides an object to the first electrode when the surgical section moves toward the object, and the first electrode is disposed on the first surface such that part of the first electrode is exposed from a bottom of the V-shaped groove.

4. The instrument according to claim 3, wherein the second electrode and the third electrode are disposed so as to extend from a base end of the surgical section to the tip end of the surgical section in a longitudinal direction of the surgical section and to be symmetrical with respect to the V-shaped groove in the longitudinal direction of the surgical section.

5. The instrument according to claim 4, wherein the area of the second electrode is substantially equal to the area of the third electrode.

6. The instrument according to claim 1, wherein the insertion section comprises an inside channel, through which an endoscope is insertable.

7. The instrument according to claim 1, wherein the surgical section is configured to move forward and backward relative to the insertion section in a direction of the central axis, such that the surgical section is projected or retracted from the tip end part of the insertion section in the direction of the central axis.

8. The instrument according to claim 1, wherein the vein keeper comprises a blood vessel holding base configured to hold the blood vessel, and
the surgical section is configured to move forward and backward in a direction of the central axis such that the surgical section is opposed to the blood vessel holding base in the radial direction of the insertion section.

* * * * *